United States Patent [19]

Steinbüchel et al.

[11] Patent Number: 6,011,144
[45] Date of Patent: Jan. 4, 2000

[54] PHA E AND PHA C COMPONENTS OF POLY (HYDROXY FATTY ACID) SYNTHASE FROM THIOCAPSA PFENNIGII

[75] Inventors: Alexander Steinbüchel, Altenberge; Mathias Liebergesell, Göttingen, both of Germany; Henry Valentin, Chesterfield, Mo.; Andreas Pries, Bad Reichenhall, Germany

[73] Assignee: Monsanto Company, St. Louis, Mo.

[21] Appl. No.: 08/809,286

[22] PCT Filed: Sep. 15, 1995

[86] PCT No.: PCT/DE95/01279

§ 371 Date: Jul. 3, 1997

§ 102(e) Date: Jul. 3, 1997

[87] PCT Pub. No.: WO96/08566

PCT Pub. Date: Mar. 21, 1996

[30] Foreign Application Priority Data

Sep. 16, 1994 [DE] Germany ............................ 44 33 134

[51] Int. Cl.⁷ .......................... C12N 15/31; C07K 14/195
[52] U.S. Cl. .......................... 536/23.2; 536/23.7
[58] Field of Search .................... 536/23.2, 23.7

[56] References Cited

PUBLICATIONS

Liebergesell et al., Appl. Microbiol. Biotechnol. 40:292–300 (1993).

Valentin et al., Appl. Microbiol. Biotechnol. 40:710–716 (1994).

Kimmel., "Identification and Characterization of Specific Clones: Strategy for Confirming the Validity of Presumptive Clones," in *Methods in Enzymology: Guide to Molecular Cloning Techniques*, vol. 152, Academic Press: New York, pp. 507–511 (1987).

Greene et al., "Subcloning," in *Methods in Enzymology: Guide to Molecular Cloning Techniques*, vol. 152, Academic Press: New York, pp. 512–522 (1987).

Barnes., "Sequencing DNA with Dideoxyribonucleotides as Chain Terminators: Hints and Strategies for Big Projects," in *Methods in Enzymology: Guide to Molecular Cloning Techniques*, vol. 152, Academic Press: New York, pp. 538–556 (1987).

New England Biolabs Catalog 1992. New England Biolabs, Beverly, MA. p. 32.

*Primary Examiner*—Johnny F. Railey, II
*Attorney, Agent, or Firm*—Gary Bond; Arnold White & Durkee

[57] ABSTRACT

The present invention relates to a process for the production of poly (hydroxy fatty acids) as well as recombinant bacterial strains for carrying out the process. In addition, new poly(hydroxy fatty acids) and new substrates for the production of conventional and new poly(hydroxy fatty acids) are described. Moreover, the invention also relates to a DNA fragment, which codes for a PhaE and a PhaC component of the poly(hydroxy fatty acid) synthase from *Thiocapsa pfennigii*, as well as the corresponding poly (hydroxy fatty acid) synthase protein.

4 Claims, 23 Drawing Sheets

1 GGATCCTGGT CGCGAGCGCG CCGCCCAGCC ACCTGCCGGC GCGCCCCGCC

GGGACCGCTC GAGGACGCCT CGCGAAGGCT CTAGGGGCTG TATCTTCAAG

101 AGTCTACGCC CCTTTGTTGC AGTGCACAAA TTTCCGTGCT AGCTTCATGC
         "-35"

phaE
TATCACGCCC CAGAC*GAGGA AGA*TTCACCG TGAACGATAC GGCCAACAAG
              S/D              V   N   D   T   A   N   K 201 ACCAGCGACT GGCTGGACAT CCAACGCAAG TACTGGGAGA CCTGGTCGGA
    T   S   D   W   L   D   I   Q   R   K   Y   W   E   T   W   S   E GCTCGGCCGC AAGACCTTGG GTCTGGAGAA GACCCCGGCC AATCCTTGGG
L   G   R   K   T   L   G   L   E   K   T   P   A   N   P   W   A 301 CCGGCGCCCT CGATCATTGG TGGCAGACGG TCTCGCCCGC CGCCCCCAAC
    G   A   L   D   H   W   W   Q   T   V   S   P   A   A   P   N GACCTGGTTC GCGACTTCAT GGAGAAGCTC GCCGAGCAGG GCAAGGCCTT
D   L   V   R   D   F   M   E   K   L   A   E   Q   G   K   A   F 401 CTTCGGCCTC ACCGACTACT TCACGAAGGG CCTCGGCGGC AGTAGCGGTA
    F   G   L   T   D   Y   F   T   K   G   L   G   G   S   S   G   T CGCAGGGCTG GGACACCCTC TCGAAGACCA TCGACGACAT GCAAAAGGCC
Q   G   W   D   T   L   S   K   T   I   D   D   M   Q   K   A

FIG. 1A

```
501 TTCGCCAGCG GCCGGATCGA AGGCGACGAG ACCTTCCGCC GCCTGATGGC
     F  A  S  G   R  I  E   G  D  E   T  F  R  R   L  M  A

CTTCTGGGAG ATGCCGCTCG ACAACTGGCA GCGCACCATG TCCTCGCTGT
     F  W  E   M  P  L  D   N  W  Q   R  T  M   S  S  L  S

601 CCCCGGTGCC CGGCGACCTG CTGCGCAACA TGCCGCACGA CCAAGTCAGG
      P  V  P   G  D  L   L  R  N  M   P  H  D   Q  V  R

GACAGCGTCG ACCGCATCCT CTCGGCACCC GGGCTCGGCT ACACGCGCGA
     D  S  V  D   R  I  L   S  A  P   G  L  G  Y   T  R  E

701 GGAGCAGGCC CGCTACCAGG ATCTGATCCG CCGCTCGCTG GAGTACCAGT
     E  Q  A   R  Y  Q  D   L  I  R   R  S  L   E  Y  Q  S

CGGCCCTGAA CGAATACAAC GGCTTCTTCG GCCAGCTCGG TGTCAAGTCC
     A  L  N   E  Y  N   G  F  F  G   Q  L  G   V  K  S

801 CTCGAGCGGA TGCGCGCCTT CCTGCAGGGA CAGGCCGAGA AGGGCGTCGC
     L  E  R  M   R  A  F   L  Q  G   Q  A  E  K   G  V  A

CATCGAGTCG GCGCGCACCC TCTACGACGC CTGGGTCGGC TGCTGCGAAG
     I  E  S   A  R  T  L   Y  D  A  W   V  G   C  C  E  E

901 AGGTCTATGC CGAGGAGGTC AGCTCCGCCG ACTACGCGCA CATCCACGGC
      V  Y  A   E  E  V   S  S  A  D   Y  A  H   I  H  G

CGCCTCGTCA ACGCCCAGAT GGCCCTCAAG CAGCGCATGT CGACCATGGT
     R  L  V   N  A  Q  M   A  L  K   Q  R  M   S  T  M  V
```

FIG. 1B

```
1001 CGACGAGGTC CTCGGCGCGA TGCCGCTGCC GACCCGCAGC GAGCTGCGCA
       D  E  V   L  G  A  M   P  L  P    T  R  S    E  L  R  T

CGCTCCAGGA TCGGCTCCAG GAGTCGCGCG GCGAGGGCAA GCGCCAGCGC
      L  Q  D   R  L  Q    E  S  R  G   E  G  K   R  Q  R

1101 CAAGAGATCG AGACGCTGAA GCGGCAGGTC GCGGCCTTGG CCGGCGGCGC
      Q  E  I   E  T  L  K  R  Q  V   A  A  L    G  G  A

CCAGCCCGCG CCCCAGGCCT CCGCCCAGCC CAGCACCCGG CCCGCGCCGG
      Q  P  A   P  Q  A  S  A  Q  P    S  T  R    P  A  P  A

1201 CGACGGCCCC GGCGGCGAGC GCGGCGCCCA AGCGCAGCAC CACGACCCGC
       T  A  P   A  A  S   A  A  P  K   R  S  T   T  T  R

CGCAAGACCA CCAAGCCCAC CACCGGCCAG TGATGTCGGC CGCCCGTCCA
      R  K  T  T  K  P  T   T  G  Q   * phaC
1301 TCGCCACCAG GAGAGAGTGC CGTGTCCCCA TTCCCGATCG ACATCCGGCC
              S/D              V  S  P   F  P  I  D   I  R  P CGACAAGCTG ACCGAGGAGA TGCTGGAGTA CAGCCGCAAG CTCGGCGAGG
      D  K  L   T  E  E   M  L  E  Y   S  R  K   L  G  E  G 1401 GTATGCAGAA CCTGCTCAAG GCCGACCAGA TCGACACAGG CGTCACCCCC
       M  Q  N   L  L  K   A  D  Q  I   D  T  G   V  T  P AAGGACGTCG TCCACCGCGA GGACAAGCTG GTCCTCTACC GCTACCGGCG
      K  D  V  V   H  R  E   D  K  L   V  L  Y  R   Y  R  R
```

FIG. 1C

```
1501 CCCGGCGCAG GTGGCGACCC AGACGATCCC GCTGCTGATC GTCTACGCCC
      P  A  Q   V  A  T  Q    T  I  P    L  L  I     V  Y  A  L

TCGTCAATCG GCCCTACATG ACCGACATCC AGGAGGATCG CTCGACGATC
      V  N  R    P  Y  M    T  D  I  Q   E  D  R   S  T  I

1601 AAGGGCCTGC TCGCCACCGG TCAGGACGTC TATCTGATCG ACTGGGGCTA
      K  G  L  L   A  T  G   Q  D  V    Y  L  I  D    W  G  Y

CCCGGATCAG GCCGACCGGG CGCTGACCCT CGATGACTAC ATCAACGGCT
      P  D  Q    A  D  R  A   L  T  L    D  D  Y    I  N  G  Y

1701 ACATCGACCG CTGCGTCGAC TACCTGCGCG AGACCCACGG CGTCGACCAG
       I  D  R    C  V  D    Y  L  R  E   T  H  G   V  D  Q

GTCAACCTGC TCGGGATCTG CCAGGGCGGG GCCTTCAGCC TCTGCTACAC
      V  N  L  L   G  I  C    Q  G  G    A  F  S  L   C  Y  T

1801 GGCCCTGCAC TCCGAGAAGG TCAAAAACCT CGTCACCATG GTCACGCCGG
      A  L  H    S  E  K  V   K  N  L    V  T  M    V  T  P  V

TCGACTTCCA GACCCCGGGC AACCTGCTCT CGGCCTGGGT CCAGAACGTC
      D  F  Q    T  P  G    N  L  L  S   A  W  V    Q  N  V

1901 GACGTCGACC TGGCCGTCGA CACCATGGGC AACATCCCGG GCGAACTGCT
      D  V  D  L   A  V  D   T  M  G    N  I  P  G   E  L  L

CAACTGGACC TTCCTGTCGC TCAAGCCCTT CAGCCTGACC GGCCAGAAGT
      N  W  T    F  L  S  L   K  P  F    S  L  T    G  Q  K  Y
```

FIG. 1D

```
2001 ACGTCAACAT GGTCGACCTG CTCGACGACG AGGACAAGGT CAAGAACTTC
      V  N  M   V  D  L    L  D  D    E  D  K  V   K  N  F

CTGCGGATGG AGAAGTGGAT CTTCGACAGC CCGGACCAGG CCGGCGAGAC
      L  R  M  E  K  W  I   F  D  S    P  D  Q  A   G  E  T

2101 CTTCCGCCAG TTCATCAAGG ACTTCTACCA GCGCAACGGC TTCATCAACG
      F  R  Q   F  I  K  D  F  Y  Q   R  N  G    F  I  N  G

GCGGCGTCCT GATCGGCGAT CAGGAGGTCG ACCTGCGCAA CATCCGCTGC
      G  V  L   I  G  D    Q  E  V  D  L  R  N    I  R  C

2201 CCGGTCCTGA ACATCTACCC GATGCAGGAC CACCTGGTGC CGCCGGATGC
      P  V  L   N  I  Y  P  M  Q  D   H  L  V    P  P  D  A

CTCCAAGGCC CTCGCGGGAC TGACCTCCAG CGAGGACTAC ACGGAGCTCG
      S  K  A   L  A  G  L  T  S  S   E  D  Y    T  E  L  A

2301 CCTTCCCCGG CGGGCACATC GGCATCTACG TCAGCGGCAA GGCGCAGGAA
      F  P  G   G  H  I    G  I  Y   V  S  G  K  A  Q  E

GGAGTCACCC CGGCGATCGG CCGCTGGCTG AACGAACGCG GCTGAGCCGG
      G  V  T  P  A  I  G   R  W  L   N  E  R  G   *

2401 GTCGACCCAC CCGCTCGACG GGCGCGGCCG GCGGCATCGA AGGCCGCCGG

CCGGCGCCCA TGAGCCATCC GCGCCGCTGG CGCCCGCCCC CCGACCTTCG
```

FIG. 1E

2501 CCGCCGCACC CGCATCGCCC CCGCGGCTGG CGTACAATGA CGGTCTTCGC

GAGCGAGCCC CGCATCGTCA ACGGAGGCTG CATGGGCGCC GACCACCAAC

2601 TGCTGGCCGC GTACGACGCG CTGGCCGAGA CCTACGACGC CCACCGCGGC

CTCTTCGACA TGCGCGCCGT GCTCGAGGAC ATCTTCGCCC GCCTGCCGGC

2701 CTGCGGCACC CTCCTCGACC TCGGCTGCGG CGCCGGGGAG CCGTGCGCGC

GCGCCTTCCT CGACCGCGGC TGGCGGGTGA CCGGGGTGGA CTTCTGCCCG

2801 GCCATGCTCG CCCTCGCGGC GCGCTACGTC CCCGAGATGG AGCGGATCC

FIG. 1F

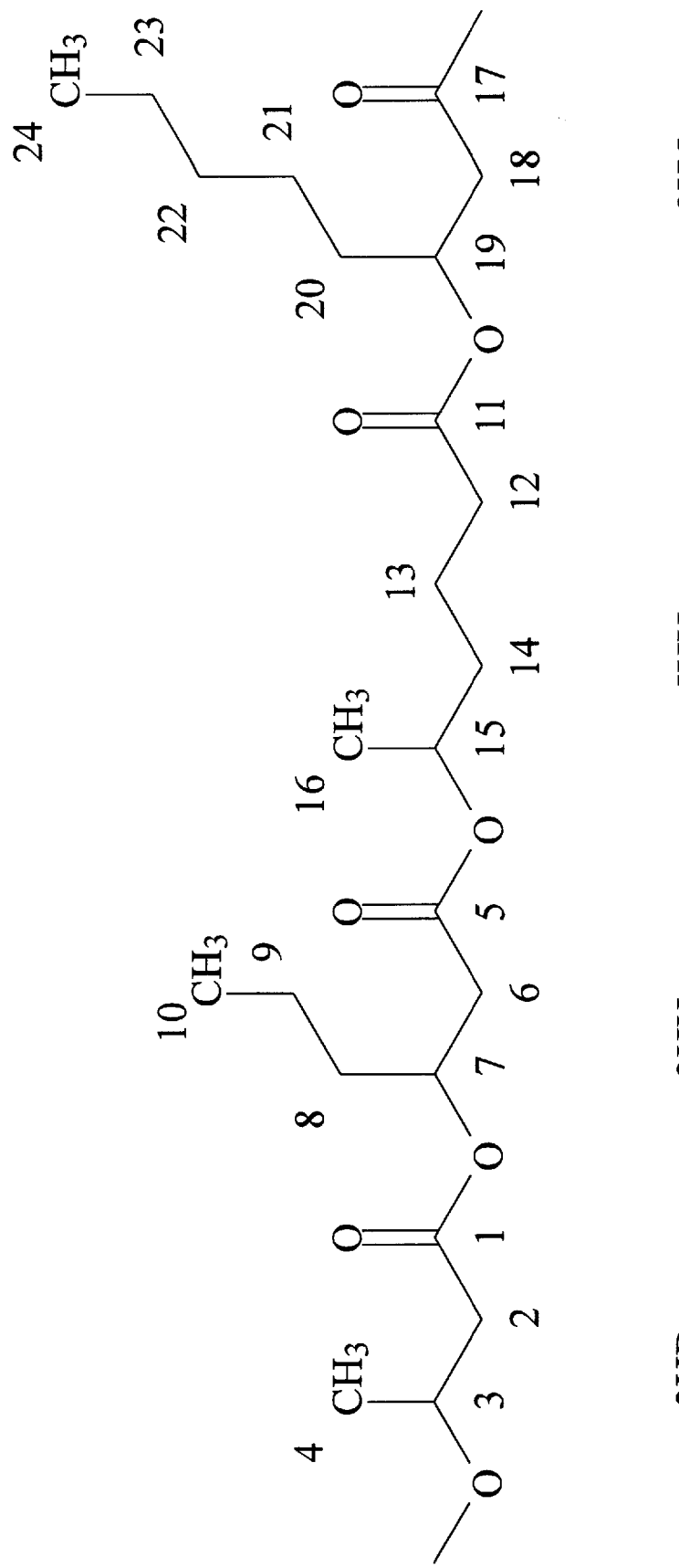

3HB  3HHx  4HHx

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 2849 base pairs
      (B) TYPE: nucleic acid
      (C) STRANDEDNESS: double
      (D) TOPOLOGY: linear (iii) HYPOTHETICAL: NO (iv) ANTI-SENSE: NO (vi) ORIGINAL SOURCE:
    (A) ORGANISM: Thiocapsa pfennigii (vii) IMMEDIATE SOURCE:
    (B) CLONE: Pseudomonas putida SK 6691/Alcaligenes
        eutrophus SK 6891

(xi) SEQUENCE DESCRIPTION: SEQ ID NO: 1:

```
GGATCCTGGT CGCGAGCGCG CCGCCCAGCC ACCTGCCGGC GCGCCCCGCC GGGACCGCTC      60

GAGGACGCCT CGCGAAGGCT CTAGGGGCTG TATCTTCAAG AGTCTACGCC CCTTTGTTGC     120

AGTGCACAAA TTTCCGTGCT AGCTTCATGC TATCACGCCC CAGACGAGGA AGATTCACCG     180

TGAACGATAC GGCCAACAAG ACCAGCGACT GGCTGGACAT CCAACGCAAG TACTGGGAGA     240

CCTGGTCGGA GCTCGGCCGC AAGACCTTGG GTCTGGAGAA GACCCCGGCC AATCCTTGGG     300

CCGGCGCCCT CGATCATTGG TGGCAGACGG TCTCGCCCGC CGCCCCCAAC GACCTGGTTC     360

GCGACTTCAT GGAGAAGCTC GCCGAGCAGG GCAAGGCCTT CTTCGGCCTC ACCGACTACT     420

TCACGAAGGG CCTCGGCGGC AGTAGCGGTA CGCAGGGCTG GACACCCTC TCGAAGACCA      480

TCGACGACAT GCAAAAGGCC TTCGCCAGCG GCCGGATCGA AGGCGACGAG ACCTTCCGCC     540

GCCTGATGGC CTTCTGGGAG ATGCCGCTCG ACAACTGGCA GCGCACCATG TCCTCGCTGT     600

CCCCGGTGCC CGGCGACCTG CTGCGCAACA TGCCGCACGA CCAAGTCAGG GACAGCGTCG     660

ACCGCATCCT CTCGGCACCC GGGCTCGGCT ACACGCGCGA GGAGCAGGCC CGCTACCAGG     720

ATCTGATCCG CCGCTCGCTG GAGTACCAGT CGGCCCTGAA CGAATACAAC GGCTTCTTCG     780

GCCAGCTCGG TGTCAAGTCC CTCGAGCGGA TGCGCGCCTT CCTGCAGGGA CAGGCCGAGA     840

AGGGCGTCGC CATCGAGTCG GCGCGCACCC TCTACGACGC CTGGGTCGGC TGCTGCGAAG     900

AGGTCTATGC CGAGGAGGTC AGCTCCGCCG ACTACGCGCA CATCCACGGC CGCCTCGTCA     960

ACGCCCAGAT GGCCCTCAAG CAGCGCATGT CGACCATGGT CGACGAGGTC CTCGGCGCGA    1020

TGCCGCTGCC GACCCGCAGC GAGCTGCGCA CGCTCCAGGA TCGGCTCCAG GAGTCGCGCG    1080

GCGAGGGCAA CGCCAGCGC CAAGAGATCG AGACGCTGAA GCGGCAGGTC GCGGCCTTGG     1140

CCGGCGGCGC CCAGCCCGCG CCCCAGGCCT CCGCCCAGCC CAGCACCCGG CCCGCGCCGG    1200

CGACGGCCCC GGCGGCGAGC GCGGCGCCCA AGCGCAGCAC CACGACCCGC CGCAAGACCA    1260

CCAAGCCCAC CACCGGCCAG TGATGTCGGC CGCCCGTCCA TCGCCACCAG GAGAGAGTGC    1320

CGTGTCCCCA TTCCCGATCG ACATCCGGCC CGACAAGCTG ACCGAGGAGA TGCTGGAGTA    1380

CAGCCGCAAG CTCGGCGAGG GTATGCAGAA CCTGCTCAAG GCCGACCAGA TCGACACAGG    1440

CGTCACCCCC AAGGACGTCG TCCACCGCGA GGACAAGCTG GTCCTCTACC GCTACCGGCG    1500

CCCGGCGCAG GTGGCGACCC AGACGATCCC GCTGCTGATC GTCTACGCCC TCGTCAATCG    1560

GCCCTACATG ACCGACATCC AGGAGGATCG CTCGACGATC AAGGGCCTGC TCGCCACCGG    1620

TCAGGACGTC TATCTGATCG ACTGGGGCTA CCCGGATCAG GCCGACCGGG CGCTGACCCT    1680

CGATGACTAC ATCAACGGCT ACATCGACCG CTGCGTCGAC TACCTGCGCG AGACCCACGG    1740

CGTCGACCAG GTCAACCTGC TCGGGATCTG CCAGGGCGGG GCCTTCAGCC TCTGCTACAC    1800

GGCCCTGCAC TCCGAGAAGG TCAAAAACCT CGTCACCATG GTCACGCCGG TCGACTTCCA    1860

GACCCCGGGC AACCTGCTCT CGGCCTGGGT CCAGAACGTC GACGTCGACC TGGCCGTCGA    1920

CACCATGGGC AACATCCCGG CGAACTGCT CAACTGGACC TTCCTGTCGC TCAAGCCCTT     1980

CAGCCTGACC GGCCAGAAGT ACGTCAACAT GGTCGACCTG CTCGACGACG AGGACAAGGT    2040

CAAGAACTTC CTGCGGATGG AGAAGTGGAT CTTCGACAGC CCGGACCAGG CCGGCGAGAC    2100
```

```
CTTCCGCCAG TTCATCAAGG ACTTCTACCA GCGCAACGGC TTCATCAACG GCGGCGTCCT    2160

GATCGGCGAT CAGGAGGTCG ACCTGCGCAA CATCCGCTGC CCGGTCCTGA ACATCTACCC    2220

GATGCAGGAC CACCTGGTGC CGCCGGATGC CTCCAAGGCC CTCGCGGGAC TGACCTCCAG    2280

CGAGGACTAC ACGGAGCTCG CCTTCCCCGG CGGGCACATC GGCATCTACG TCAGCGGCAA    2340

GGCGCAGGAA GGAGTCACCC CGGCGATCGG CCGCTGGCTG AACGAACGCG GCTGAGCCGG    2400

GTCGACCCAC CCGCTCGACG GGCGCGGCCG GCGGCATCGA AGGCCGCCGG CCGGCGCCCA    2460

TGAGCCATCC GCGCCGCTGG CGCCCGCCCC CCGACCTTCG CCGCCGCACC CGCATCGCCC    2520

CCGCGGCTGG CGTACAATGA CGGTCTTCGC GAGCGAGCCC CGCATCGTCA ACGGAGGCTG    2580

CATGGGCGCC GACCACCAAC TGCTGGCCGC GTACGACGCG CTGGCCGAGA CCTACGACGC    2640

CCACCGCGGC CTCTTCGACA TGCGCGCCGT GCTCGAGGAC ATCTTCGCCC GCCTGCCGGC    2700

CTGCGGCACC CTCCTCGACC TCGGCTGCGG CGCCGGGGAG CCGTGCGCGC GCGCCTTCCT    2760

CGACCGCGGC TGGCGGGTGA CCGGGGTGGA CTTCTGCCCG GCCATGCTCG CCCTCGCGGC    2820

GCGCTACGTC CCCGAGATGG AGCGGATCC                                      2849
```

(2) INFORMATION FOR SEQ ID NO: 2:

(i) SEQUENCE CHARACTERISTICS:
        (A) LENGTH: 367 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 2:

```
Val Asn Asp Thr Ala Asn Lys Thr Ser Asp Trp Leu Asp Ile Gln Arg
 1               5                  10                  15

Lys Tyr Trp Glu Thr Trp Ser Glu Leu Gly Arg Lys Thr Leu Gly Leu
             20                  25                  30

Glu Lys Thr Pro Ala Asn Pro Trp Ala Gly Ala Leu Asp His Trp Trp
         35                  40                  45

Gln Thr Val Ser Pro Ala Ala Pro Asn Asp Leu Val Arg Asp Phe Met
     50                  55                  60

Glu Lys Leu Ala Glu Gln Gly Lys Ala Phe Phe Gly Leu Thr Asp Tyr
 65                  70                  75                  80

Phe Thr Lys Gly Leu Gly Gly Ser Ser Gly Thr Gln Gly Trp Asp Thr
                 85                  90                  95

Leu Ser Lys Thr Ile Asp Asp Met Gln Lys Ala Phe Ala Ser Gly Arg
            100                 105                 110

Ile Glu Gly Asp Glu Thr Phe Arg Arg Leu Met Ala Phe Trp Glu Met
        115                 120                 125

Pro Leu Asp Asn Trp Gln Arg Thr Met Ser Ser Leu Ser Pro Val Pro
    130                 135                 140

Gly Asp Leu Leu Arg Asn Met Pro His Asp Gln Val Arg Asp Ser Val
145                 150                 155                 160

Asp Arg Ile Leu Ser Ala Pro Gly Leu Gly Tyr Thr Arg Glu Glu Gln
                165                 170                 175

Ala Arg Tyr Gln Asp Leu Ile Arg Arg Ser Leu Glu Tyr Gln Ser Ala
            180                 185                 190

Leu Asn Glu Tyr Asn Gly Phe Phe Gly Gln Leu Gly Val Lys Ser Leu
        195                 200                 205
```

```
Glu Arg Met Arg Ala Phe Leu Gln Gly Gln Ala Glu Lys Gly Val Ala
    210                 215                 220

Ile Glu Ser Ala Arg Thr Leu Tyr Asp Ala Trp Val Gly Cys Cys Glu
225                 230                 235                 240

Glu Val Tyr Ala Glu Val Ser Ser Ala Asp Tyr Ala His Ile His
                    245                 250                 255

Gly Arg Leu Val Asn Ala Gln Met Ala Leu Lys Gln Arg Met Ser Thr
                260                 265                 270

Met Val Asp Glu Val Leu Gly Ala Met Pro Leu Pro Thr Arg Ser Glu
                275                 280                 285

Leu Arg Thr Leu Gln Asp Arg Leu Gln Glu Ser Arg Gly Glu Gly Lys
290                 295                 300

Arg Gln Arg Gln Glu Ile Glu Thr Leu Lys Arg Gln Val Ala Ala Leu
305                 310                 315                 320

Ala Gly Gly Ala Gln Pro Ala Pro Gln Ala Ser Ala Gln Pro Ser Thr
                325                 330                 335

Arg Pro Ala Pro Ala Thr Ala Pro Ala Ala Ser Ala Ala Pro Lys Arg
                340                 345                 350

Ser Thr Thr Thr Arg Arg Lys Thr Thr Lys Pro Thr Thr Gly Gln
                355                 360                 365
```

(2) INFORMATION FOR SEQ ID NO: 3:

(i) SEQUENCE CHARACTERISTICS:
    (A) LENGTH: 357 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 3:

```
Val Ser Pro Phe Pro Ile Asp Ile Arg Pro Asp Lys Leu Thr Glu Glu
1               5                   10                  15

Met Leu Glu Tyr Ser Arg Lys Leu Gly Glu Gly Met Gln Asn Leu Leu
                20                  25                  30

Lys Ala Asp Gln Ile Asp Thr Gly Val Thr Pro Lys Asp Val Val His
                35                  40                  45

Arg Glu Asp Lys Leu Val Leu Tyr Arg Tyr Arg Pro Ala Gln Val
50                  55                  60

Ala Thr Gln Thr Ile Pro Leu Leu Ile Val Tyr Ala Leu Val Asn Arg
65                  70                  75                  80

Pro Tyr Met Thr Asp Ile Gln Glu Asp Arg Ser Thr Ile Lys Gly Leu
                85                  90                  95

Leu Ala Thr Gly Gln Asp Val Tyr Leu Ile Asp Trp Gly Tyr Pro Asp
                100                 105                 110

Gln Ala Asp Arg Ala Leu Thr Leu Asp Asp Tyr Ile Asn Gly Tyr Ile
                115                 120                 125

Asp Arg Cys Val Asp Tyr Leu Arg Glu Thr His Gly Val Asp Gln Val
                130                 135                 140

Asn Leu Leu Gly Ile Cys Gln Gly Gly Ala Phe Ser Leu Cys Tyr Thr
145                 150                 155                 160

Ala Leu His Ser Glu Lys Val Lys Asn Leu Val Thr Met Val Thr Pro
                165                 170                 175

Val Asp Phe Gln Thr Pro Gly Asn Leu Leu Ser Ala Trp Val Gln Asn
                180                 185                 190

Val Asp Val Asp Leu Ala Val Asp Thr Met Gly Asn Ile Pro Gly Glu
```

|     | 195 |     |     |     | 200 |     |     |     |     | 205 |     |     |
|-----|-----|-----|-----|-----|-----|-----|-----|-----|-----|-----|-----|-----|
| Leu | Leu | Asn | Trp | Thr | Phe | Leu | Ser | Leu | Lys | Pro | Phe | Ser | Leu | Thr | Gly |
|     | 210 |     |     |     |     | 215 |     |     |     |     | 220 |     |

Leu Leu Asn Trp Thr Phe Leu Ser Leu Lys Pro Phe Ser Leu Thr Gly
    210                     215                 220

Gln Lys Tyr Val Asn Met Val Asp Leu Leu Asp Asp Glu Asp Lys Val
225             230                 235             240

Lys Asn Phe Leu Arg Met Glu Lys Trp Ile Phe Asp Ser Pro Asp Gln
                245                 250                 255

Ala Gly Glu Thr Phe Arg Gln Phe Ile Lys Asp Phe Tyr Gln Arg Asn
            260                 265                 270

Gly Phe Ile Asn Gly Gly Val Leu Ile Gly Asp Gln Glu Val Asp Leu
        275                 280                 285

Arg Asn Ile Arg Cys Pro Val Leu Asn Ile Tyr Pro Met Gln Asp His
    290                 295                 300

Leu Val Pro Pro Asp Ala Ser Lys Ala Leu Ala Gly Leu Thr Ser Ser
305             310                 315                 320

Glu Asp Tyr Thr Glu Leu Ala Phe Pro Gly Gly His Ile Gly Ile Tyr
            325                 330                 335

Val Ser Gly Lys Ala Gln Glu Gly Val Thr Pro Ala Ile Gly Arg Trp
            340                 345                 350

Leu Asn Glu Arg Gly
            355

PHA E AND PHA C COMPONENTS OF POLY (HYDROXY FATTY ACID) SYNTHASE FROM THIOCAPSA PFENNIGII

The present application is a national stage application of PCT/DE95/01279, filed on Sep. 15, 1995.

BACKGROUND OF THE INVENTION

The present invention relates to a process for the production of poly(hydroxy acids) by means of recombinant bacteria which contain and express at least one fragment of the gene of poly(hydroxy fatty acid) synthase from *Thiocapsa pfennigii* and which are selected from the group comprising: *Pseudomonas putida* GPp104 (pHP1014::E156), *Alcaligenes eutrophus* PHB 4 (pHP1014::EIS6), *Pseudomonas putida* GPp104 (pHP1014::B28+) [DSM #9417] and *Alcaligenes eutrophus* PHB 4 (pHP1014: B28+) [DSM #9418], whereby the bacteria are cultivated in a mineral medium under aerobic conditions, whereby one offers the bacteria at least one substrate carbon source which is selected from the group consisting of: levulinic acid, salts of levulinic acid, esters of levulinic acid, lactones of levulinic acid, substituted levulinic acid or, as the case may be, its derivatives; 5-hydroxyhexanoic acid, its salts, esters and lactones; 4-hydroxyheptanoic acid, its salts, esters and lactones; 4-hydroxyoctanoic acid, its salts, esters and lactones, their halogenated derivatives as well as their mixtures; one incubates the bacteria for a certain time with the carbon source; and one isolates the poly(hydroxy fatty acid) polymers that have been synthesized by the bacteria;

a recombinant bacterial strain characterized by the feature that the bacterial strain is selected from the group which comprises *Pseudomonas putida* GPp104 (pHP1014::B28+) [DSM #9417] and *Alcaligenes eutrophus* PHB 4 (pHP1014::B28+) [DSM #9418];

a poly(hydroxy fatty acid) produced by any one of the previously described processes;

and a DNA fragment which codes for a pha E component and a pha C component of the poly(hydroxy fatty acid) synthase from *Thiocapsa pfennigii* characterized by the feature that it has at least the nucleotide sequence of sequence sections 180 through 1280 (phaE) and 1322 through 2392 (phaC) of the DNA sequence SEQ ID NO: 1.

In this age of increasing environmental awareness, there are increasing attempts in industry and science to produce biodegradable polymers. In this regard, these new types of environmentally compatible polymers should essentially have the same properties as those polymers which, for decades, have been prepared via organic chemical synthesis.

In particular in this connection, the ability to process the new types of biodegradable polymers ought to be provided in a similar manner to the processing of conventional plastics using the same methods such as, for example, extrusion, injection molding, injection compression, foaming, etc.

A big disadvantage of organically synthesized plastics is, however, that many of these plastics have enormous biological half-lives or, as the case may be, they cannot be disposed of in garbage dumps or in garbage incineration plants in a non-harmful manner but, rather, aggressive gases are frequently produced such as, for example, in the case of poly(vinyl chloride) which liberates hydrogen chloride gas during incineration.

A first step in the direction of success with environmentally compatible materials was achieved by means of synthetic substances, e.g. the paraffin-like polymers polyethylene and polypropylene since these essentially release only $CO_2$ and water on incineration.

In addition, many attempts have also been made by means of so-called replaceable raw materials such as, e.g. plants that contain a lot of polysaccharide such as potatoes, corn, wheat, beans, peas or similar materials, to obtain the naturally occurring polysaccharides in these plants and to prepare polymers from them which are usable in plastics technology and which are biodegradable.

However, in the case of such polymer materials comprising replaceable raw materials, one is essentially relying on the natural quality of the polymers that occur in these higher plants and only the relatively complex processes of classical cultivation and modern gene technology offer themselves for modification at the genetic level.

An essential further step in the direction of naturally occurring polymers, which are very similar to synthetic thermoplastics, was brought about by the discovery of poly(3-hydroxybutyric acid) by Lemoigne in 1926 [Lemoigne, M. (1926) Products of the dehydration and polymerization of β-oxybutyric acid, *Bull Soc. Chim. Biol.* (Paris) 8: 770–782]. The discovery by Lemoigne can be considered to have paved the way for the further development of modern poly(hydroxy fatty acids) which are also designated polyhydroxyalkanoates and represent chemically linear esters of hydroxy fatty acids and hence, ultimately, polyesters.

In the eighties and, especially, in the last five years, further hydroxy fatty acids have been described as components of the poly(hydroxy fatty acids) (PHF) that occur in nature. In this connection, the hydroxyl group of these PHF is usually located in the 3' position. The aliphatic side chains are either saturated or singly or doubly unsaturated. They are thus non-branched or branched and they can be substituted by functional groups such as, for example, halogen atoms, preferably bromine, iodine and chlorine, or cyano groups, ester groups, carboxyl groups or even cyclic aliphatic groups and even aromatic. In some hydroxy fatty acids, the hydroxyl group is also located in the 4' or 5' position.

Poly(hydroxy fatty acids) have been detected previously in gram positive and gram negative groups of bacteria, aerobic and anaerobic groups of bacteria, heterotrophic and autotrophic groups of bacteria, eubacteria and archaebacteria and in anoxygenic and oxygenic photosynthetic groups of bacteria and therefore in virtually all important groups of bacteria. Thus the capability of synthesizing such polyesters apparently does not represent any specially demanding or rare biochemical metabolism. Biosynthesis of the PHF usually sets in when a usable source of carbon is present in excess with the simultaneous deficiency of another nutrient component. In this way, a nitrogen deficiency, a phosphorus deficiency, a sulfur deficiency, an iron deficiency, a potassium deficiency, a magnesium deficiency or an oxygen deficiency can trigger PHF synthesis in bacteria [Anderson, A. J. and Dawes, E. A. (1990) Occurrence, metabolism, metabolic role and industrial uses of bacterial polyhydroxyalkanoates, Microbial. Rev. 54: 450–472; Steinbüchel, A. (1991) Polyhydroxyalkanoic acids: In: D. Byrom (editor) Biomaterials, Macmillan Press, New York, pages 123–213]. In most bacteria, PHF are deposited in the form of inclusions or grana in cytoplasm, whereby the dry mass of the cell can amount to up to a proportion of 95% by weight.

In eukaryotes, only poly(3-hydroxybutyric acid) has previously been demonstrated as the single PHF. This polyester arises in yeasts such as, for example, *Saccharomyces* cerevisiae, various plants, e.g. cauliflower, various organs from animals, e.g. the liver and also in humans, e.g. in blood plasma [Reusch, R N. 1992, Biological complexes of polyhydroxybutyrate, *FEMS Microbiol. Rev.* 103: 119–130]. However, in contradistinction to prokaryotes, the proportion of poly(3-hydroxybutyric acid) in eukaryotes is maximally 0.1% by weight. Inclusions in the form of grana, in the manner in which they occur in prokaryotes, are not known in eukaryotes. As a rule, the eukaryotic PHF are not usually present in free form, either but the polyester is present either linked to other proteins or in the form of a complex which spans the cytoplasm membrane together with calcium ions and polyphosphate molecules.

Thus, only the production of PHF in bacteria is of interest for industrial biotechnological purposes.

The biosynthesis of PHF in bacteria can be subdivided into three phases.

In phase I, the carbon source, which is offered to the bacteria in the medium, is first taken up in the bacterial cells. Either special uptake transportation systems have to exist for the corresponding carbon source or the cells are cultivated under conditions which produce a certain artificial permeability of the cytoplasm membrane with respect to the carbon source. Some non-ionic carbon sources, for example fatty acids in their non-dissociated form, can also get into the cells via passive diffusion.

In phase II, the absorbed carbon source is transformed into a suitable substrate for the particular enzyme which is capable of producing PHF. This enzyme is generally designated poly(hydroxy fatty acid) synthase. Here, numerous more or less complex reaction sequences are conceivable, which can include both anabolic enzymes and catabolic enzymes in the reaction pathway, and these have been demonstrated already, too.

Phase III comprises the linking together of monomeric precursors to give the polyester. This reaction is catalyzed by the enzyme PHF synthase which represents the key enzyme for the biosynthesis of PHF. These enzymes are linked to the PHF grana and they are located there on the surface. Engendered by the very low specificity of most of the PHF syntheses that have previously been examined in this regard and which arise in differing species, the biosynthesis of a plurality of different PHF is possible. Previously, only the co-enzyme A-thioesters of hydroxy fatty acids have been detected in the form of monomeric, bio-synthetically active precursors. As has been shown above, PHF synthase is the key enzyme for PHF synthesis.

After the structure gene of the PHF synthase from *Alcaligenes eutrophus* had been cloned and synthesized in three different laboratories independently of one another, the structure genes for the key enzyme from approximately 20 different bacteria were cloned [Slater, S. C., Voige, H. and Dennis, D. E. (1988) Cloning and expressing *Escherichia coli* of the *Alcaligenes eutrophus* H16 poly β-hydroxybutyrate bio-synthetic pathway, *J. Bacteriol.* 170: 4431–4436; Schubert, P., Steinbüchel, A. and Schlegel, H. G. (1988) Cloning of the *Alcaligenes eutrophus* gene for synthesis of poly-β-hydroxybutyric acid and synthesis of PHB in *Escherichia coli, J. Bacteriol.* 170: 5837–5847; Peoples, O. P. and Sinskey, A. J. (1989) Poly-β-hydroxybutyrate biosynthesis and *Alcaligenes eutrophus* H16. Identification and characterization of the PHB polymerase gene (phbC), *J. Biol Chem.* 264: 15298–15303].

At that time, the nucleotide sequences of at least 12 poly(hydroxy fatty acid) synthase genes (PHF synthase genes) were determined. Because of the primary structures of the enzymes, that were derived from this, and because of physiological data, three different types of PHF synthases can now be distinguished. Type I is represented by the PHF synthase from the *Alcaligenes eutrophus* bacterium which has been examined most thoroughly of all in regard to PHF metabolism and which has a molecular weight of 63,940 and catalyzes the synthesis of PHF from hydroxy fatty acids with a short chain length. In addition to 3-hydroxyvaleric acid and 5-hydroxyvaleric acid are also incorporated into a copolyester comprising different hydroxy fatty acid subunits.

Type II is represented by the PHF synthase from *Pseudomomans oleovarans*. This enzyme has a similar size to that of the type I PHF synthases (molecular mass 62,400); however, it differs considerably relative to the substrate specificity of the type I PHF synthases. It is capable of incorporating only 3-hydroxybutyric fatty acids of medium chain length into PHF. 4-hydroxy fatty acids and 5-hydroxy fatty acids and 3-hydroxybutyric acid, by contrast, are not incorporated into the bio-synthetic polyesters. However, the specificity of the enzyme is still so broad that approximately 50 different 3-hydroxy fatty acids can be processed as substrates.

Type III is represented by the PHF synthase from *Chromatium vinosum*. This enzyme resembles the type I PHF synthases from the point of view of substrate specificity. However, it has a distinctly lower molecular mass (approximately 39,730) and needs a second protein in order to be catalytically active.

To the extent that PHF have previously been isolated from bacteria, these do have extremely interesting properties: they are thermoplastically deformable, water-insoluble, biodegradable, non-toxic and optically active provided that they are not homopolyesters of ω-fatty acids. It has also been shown in the case of poly(3-hydroxybutyric acid) that it is bio-compatible and that it has piezoelectric properties.

It has been shown for poly(3-hydroxybutyric acid) [poly (3HB)] and for the copolyester poly(3-hydroxybutyric acid-co-3-hydroxy-valeric acid) [poly(3HB-co-3HV)] that these polymers can be processed with conventional injection molding processes, extrusion blowing processes and injection blowing processes as well as by fiber spinning techniques.

Only two poly(hydroxy fatty acids), namely the homopolyester poly(3HB) and the copolyester poly(3HB-co-3HV), have advanced thus far to large scale production maturity. The copolymer is marketed under the trade name "Biopol".

The production of these biopolymers is disclosed in EP-A 69 497. Production of the polymer is carried out in the form of a two-stage fed-batch process in a 35 m$^3$ air-lift reactor and in tubular kettle reactors with working volumes of up to 200 m$^3$ with a double mutant of *Alcaligenes eutrophus* as the production organism and with glucose and propionic acid as the carbon sources together with phosphate limitation [Byrom, D. (1990) Industrial production of copolymer from *Alcaligenes eutrophus*, In: Dawes, E. A. (editor) Novel biodegradable microbial polymers, pages 113–117, Kluwer Academic Publishers, Doordrecht]. The first stage serves for the growth of bacterial cells to high densities and lasts approximately 48 hours, whereby only glucose is offered as the substrate. In the second stage, the cells are grown with phosphate limitation and with glucose and propionic acid as the precursors for the 3-hydroxyvaleric acid component; cell densities of more than 100 g of dry cell mass per liter with a PHF proportion of more than 70% by weight are achieved after a further 40 to 50 hours of cultivation. The cells are then treated with an enzyme cocktail, which essentially comprises lysozyme, proteases and other hydrolytic enzymes, as a result of which the PHF grana are released. The grana sediment on the bottom of the reactor and are collected from there, washed, dried, melted, extruded and granulated.

This PHF is currently produced in a production quantity of approximately 300 metric tons on an annual basis. Although these microbially produced biopolymers, poly (3HB) and poly(3HB-co-3HV), have good properties and can be processed with the methods that are usual in plastics technology, their production is, on the one hand, still very expensive and, on the other hand, the copolymer contains only two monomeric sub-units so that the total properties of the polymer, that is produced, can be controlled only via these two quantities and thus precise control in regard to flexibility, processability in plastics technology plants, resistance to certain solvents, etc. cannot be carried out in fine controlling steps.

Although 3-hydroxyvaleric acid confers good flexibility or, as the case may be, processability on PHF, it has been found that, for example, the component 4-hydroxyvaleric acid, which can additionally be present in the PHF which are synthesized by bacteria, confers on the biopolymer, that is produced, a distinctly higher degree of flexibility than is the case with 3-hydroxyvaleric acid alone.

In the prior art, 4-hydroxyvaleric acid (4HV) has been demonstrated as a new component in bacterial PHF. Various bacteria were capable of synthesizing polyesters with this new component. These are usually copolyesters which also contain 3-hydroxybutyric acid and 3-hydroxyvaleric acid as components in addition to 4HV. However, these terpolymers could previously be produced only starting out from expensive and toxic special chemicals which were offered to the bacteria as precursor substrates or, as the case may be, as a carbon source for PHF biosynthesis.

In particular, Valentin, H. E., Schonebaüm, A. and Steinbüchel, A. (1992) *Appl. Microbiol. Biotechnol.* 36: 507–514 "Identification of 4-hydroxyvaleric acid as a constituent of bio-synthetic polyhydroxyalcanoic acids from bacteria" describe the manufacture of a terpolyester, which consists of 3-hydroxybutyric acid, 3-hydroxyvaleric acid and 4-hydroxyvaleric acid as subunits, whereby, for example, 4-hydroxyvaleric acid or 4-valerolactone is offered to an Alcaligenes strain as the sole carbon source in a batch process, a fed-batch process or a two step batch process.

SUMMARY OF THE INVENTION

The present invention relates to a process for the production of poly (hydroxy fatty acids) as well as recombinant bacterial strains for carrying out the process. In addition, new poly(hydroxy fatty acids) and new substrates for the production of conventional and new poly(hydroxy fatty acids) are described. Moreover, the invention also relates to a DNA fragment, which codes for a PhaE and a PhaC component of the poly(hydroxy fatty acid) synthase from *Thiocapsa pfennigii*, as well as the corresponding poly (hydroxy fatty acid) synthase.

DESCRIPTION OF THE FIGURES

Figures 1, 1A, 1B, 1C, 1D, 1E, 1F:
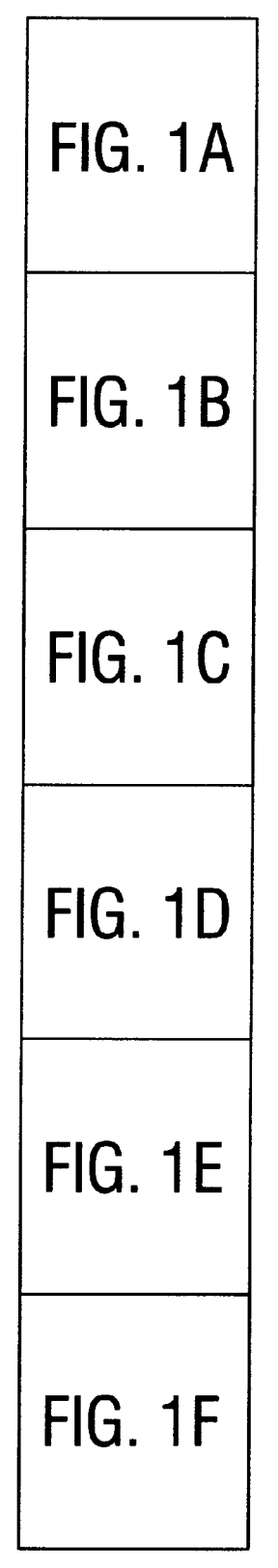

FIG. 1 shows the DNA sequence of a DNA fragment in accordance with the invention from *Thiocapsa pfennigii* and the amino acid sequence of the phaC and phae proteins. The 2.8 kb DNA fragment is obtained via the BamHI digestion of a 15.6 kb EcoRI fragment from *Thiocapsa pfennigii*. In addition, FIG. 1 shows the assignment of the amino acid sequences of the phaC and phaE proteins (using the IUPAC one letter code) to their corresponding genes phaC (DNA sequence section 1322 to 2392) and phaE (DNA sequence section 180 to 1280).

DETAILED DESCRIPTION OF THE INVENTION

Figure 2:
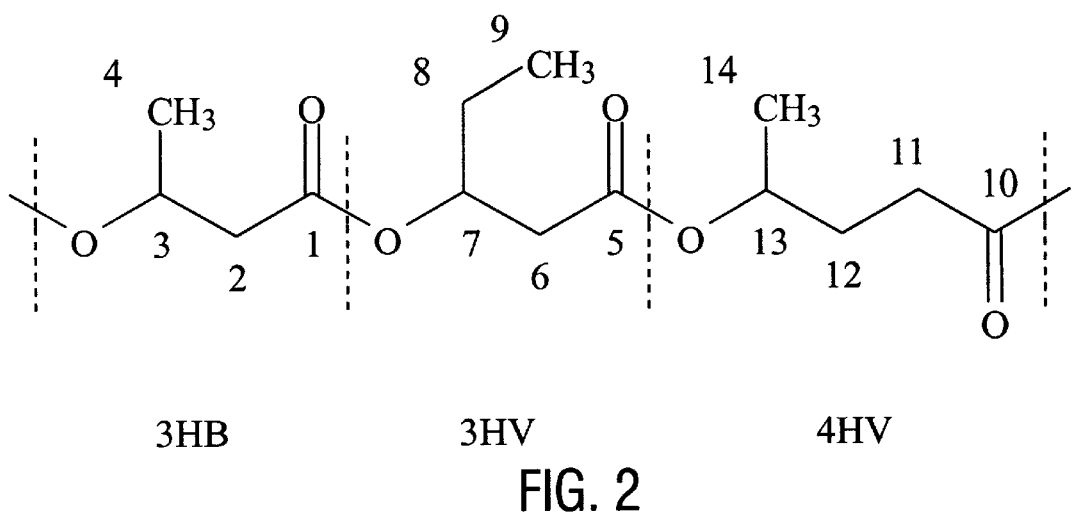
FIG. 2: Structural formula of poly(3-hydroxybutyric acid-co-3-hydroxy-valeric acid-co-4-hydroxy-valeric) [poly (3HB-co-3-HV-co-4-HV]).

However, in order to move the microorganisms, which are used in this prior art, to incorporate 4-hydroxyvaleric acid, the prior art requires the very expensive and toxic 4-hydroxyvaleric acid itself or its lactones.

Starting out from this prior art, the problem for the present invention was therefore to make PHF available with improved properties and with cheaper and non-toxic starting substances.

From a process technical standpoint, the above problem is solved by a process for the preparation of poly(hydroxy fatty acids) with at least one subunit by means of recombinant bacteria which contain and express at least one fragment of the gene of poly(hydroxy fatty acid) synthase from *Thiocapsa pfennigii* and which are selected from the group comprising: *Pseudomonas putida* GPp104 (pHP1014::E156), *Alcaligenes eutrophus* PHB 4 (pHP1014::EIS6), *Pseudomonas putida* GPp104 (plIP1014::B28+) [DSM #9417] and *Alcaligenes eutrophus* PHB 4 (pHP1014: B28+) [DSM #9418], whereby the bacteria are cultivated in a mineral medium under aerobic conditions, whereby one offers the bacteria at least one substrate carbon source which is selected from the group consisting of: levulinic acid, salts of levulinic acid, esters of levulinic acid, lactones of levulinic acid, substituted levulinic acid or, as the case may be, its derivatives; 5-hydroxyhexanoic acid, its salts, esters and lactones;

4-hydroxyheptanoic acid, its salts, esters and lactones; 4-hydroxyoctanoic acid, its salts, esters and lactones; their halogenated derivatives as well as their mixtures; one incubates the bacteria for a certain time with the carbon source; and one isolates the poly(hydroxy fatty acid) polymers that have been synthesized by the bacteria.

In regard to the recombinant bacterial strain, the problem is solved by a recombinant bacterial strain for the preparation of poly(hydroxy fatty acids), characterized by the feature that the bacterial strain is selected from the group which comprises *Pseudomonas putida* GPp104 (pHP1014::B28+) [DSM #9417] and *Alcaligenes eutrophus* PHB 4 (pHP1014::B28+) [DSM # 9418].

In regard to the poly(hydroxy fatty acid), the above problem is solved by the poly(hydroxy fatty acid) produced by any of the previously described processes. In addition, a DNA fragment which codes for a phaE component and a phaC component of the poly(hydroxy fatty acid) synthase from *Thiocapsa pfennigii* characterized by the feature that it has at least the nucleotide sequence of sequence sections 180 through 1280 (phaE) and 1322 through 2392 (phaC) of the following DNA sequence (SEQ ID NO: 1): also solves the above problem.

In accordance with the process for the preparation of poly(hydroxy fatty acids) with at least one subunit by means of recombinant bacteria which contain and express at least one fragment of the gene of poly(hydroxy fatty acid) synthase from *Thiocapsa pfennigii* and which are selected from the group comprising: *Pseudomonas putida* GPp104 (pHP1014::E156), *Alcaligenes eutrophus* PHB 4 (pHP1014::EIS6), *Pseudomonas putida* GPp104 (pHP1014::B28+) [DSM #9417] and *Alcaligenes eutrophus* PHB 4 (pHP1014: B28+) [DSM #9418], whereby the bacteria are cultivated in a mineral medium under aerobic conditions, whereby one offers the bacteria at least one substrate carbon source which is selected from the group consisting of: levulinic acid, salts of levulinic acid, esters of levulinic acid, lactones of levulinic acid, substituted levulinic acid or, as the case may be, its derivatives; 5-hydroxyhexanoic acid, its salts, esters and lactones; 4-hydroxyheptanoic acid, its salts, esters and lactones; 4-hydroxyoctanoic acid, its salts, esters and lactones; their halogenated derivatives as well as their mixtures; one incubates the bacteria for a certain time with the carbon source; and one isolates the poly(hydroxy fatty acid) polymers that have been synthesized by the bacteria., it has been possible for the first time to produce 4HV-containing polyesters starting out from levulinic acid. The chemical structure of levulinic acid is reproduced in the following formula:

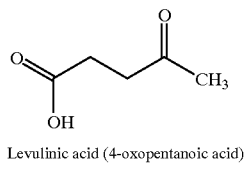

Levulinic acid (4-oxopentanoic acid)

Seen chemically, levulinic acid is 4-oxopentanoic acid which is readily soluble in water, alcohol and ether.

This is a relatively inexpensive substance, since it can be prepared from hexoses of plant origin—i.e. replaceable raw materials—e.g. by boiling with hydrochloric acid. In addition, it is also generated in a large quantity in the form of a waste product during the processing of wood and it can thus be processed further on a large industrial scale. The PHF-free mutants GPp104 of *Pseudomonas putida* (Huismann, G. W., Wonink, E., Meima, R. Kazemier, W., Terpstra, P. and Witholt, B. (1991) *J. Biol. Chem.* 266: 2191–2198) and PHB4 of *Alcaligenes eutrophus* H16 (Schlegel, H. G., Lafferty, R. and Krauss, I. (1970) *Arch. Microbiol.* 71: 283–294) are used as production organisms in accordance with the present invention into which the plasmid pHP1014::E156, which, inter alia, contains and expresses the structure group of the PHF synthase from *Thiocapsa pfennigii*, had previously been conjugatively transferred (Liebergesell, M., Mayer, F. and Steinbüchel, A. (1993) *Appl. Microbiol. Biotechnol.* 40: 292–300; Valentin, H. E., Lee, E. Y., Choi, C. Y. and Steinbüchel, A. (1994) *Appl. Microbiol. Biotechnol.* 40: 710–716). In the process in accordance with the invention use is also made of the new organisms *Pseudomonas putida* GPp104 (pHP1014::B28+), which was officially filed by BUCK-Werke GmbH & Co., Geislinger Str. 21, 73337 Bad Überkingen, Germany, at Deutsche SammLung von Mikroorganismen und Zellkulturen GmbH, Mascheroder Weg 1b, D-38124 Braunschweig under No. 9417 (*Pseudomonas putida* SK 6691—DSM 9417) on Sep. 5, 1994 in accordance with the Budapest treaty, and *Alcaligenes eutrophus* PHB 4 (pHP1014::B28+) which was officially filed at the Deutsche SammLung von Mikroorganismen (German Collection of Microorganisms), Braunschweig, under No. 9418 (*Alcaligenes eutrophus* SK 6891—DSM 9418) on Sep. 5, 1994 in accordance with the Budapest treaty.

These strains have the special property that they contain essentially exactly those DNA fragments which contain and express the genes phaE and phaC; this is because the gene products phaE and phaC are together capable of revealing PHF synthase activity.

Of course, it is well known to someone who is skilled in the art that nucleotide sequences, which carry phaE and phaC genes additionally have conventional control regions, e.g. promoters, S/D sequences or similar entities.

Using the process in accordance with the invention, it is possible to produce new 4HV-containing copolyesters which also have thermoplastic properties and which behave distinctly more flexibly than the copolyesters of the prior art.

Because of the inexpensive starting material levulinic acid which is used, the polymers could also be produced distinctly more cheaply than had previously been possible with the biotechnological processes of the prior art.

Instead of levulinic acid, use can also be made, of course, of a salt of levulinic acid or, as the case may be, a lactone of levulinic acid or, as the case may be, other derivatives, e.g. halogen derivatives, as the substrate for the production organisms of the present invention.

In addition, the inventors of the present invention have found that the recombinant bacterial strains which contain and express at least a fragment of the gene of the PHF synthase from *Thiocapsa pfennigii* are also capable of incorporating 5-hydroxy-hexanoic acid, its salts, esters and lactones into a copolyester which has been bio-synthesized by these bacteria. The preparation of 5-hydroxyhexanoic acid took place starting from 4-acetylacetic acid, which was reduced quantitatively using $NaBH_4$. The detection of 5-hydroxyhexanoic acid (5HHx) as a component took place gas chromatographically after methanolysis both in lyophilized cells and in the isolated and purified polyester. The isolated and purified polyester was subjected to $^{13}C$-NMR analysis and $^1H$-NMR analysis and the incorporation of 5 HHx was confirmed as a result of this.

By way of example, the analysis of the polyester, that was accumulated by the bacterial cells, resulted in a polyester content of more than 40% by weight of the dry mass of the cells, whereby a typical polymer contained: approximately 71 mol% of 3-hydroxybutyric acid, approximately 4 mol% of 3-hydroxyhexanoic acid, approximately 23 mol% of 5-hydroxyhexanoic acid and approximately 2 mol% of 3-hydroxy-octanoic acid.

Numerous wild type strains were also examined in regard to their capacity for being able to bio-synthesize PHF-polyesters with 5 1Hx as a subunit, starting from 5-hydroxyhexanoic acid as the carbon source. However, none of the tested strains were capable in this regard.

If 4-hydroxyheptanoic acid (4HHp) is offered as the source of carbon to the recombinant bacterial strains, that were used for the present invention, then one also finds these new components in the form of a subunit in the copolyester that is synthesized by the bacteria.

The preparation of 4-hydroxyheptanoic acid took place via the hydrolysis of γ-heptalactone with NaOH.

By way of example, the analysis of the polymer that was accumulated by the recombinant cells resulted in a polyester content of approximately 40% by weight of the dry mass of the cells. A typical polymer contained approximately 43 mol% of 3-hydroxybutyric acid, approximately 16 mol% of 3-hydroxyvaleric acid, approximately 27 mol% of 3-hydroxyhexanoic acid, approximately 5 mol% of 3-hydroxyheptanoic acid, approximately 6 mol% of 4-hydroxyheptanoic acid and approximately 6 mol% of 3-hydroxyoctanoic acid.

Numerous wild type strains were examined in regard to their capacity for being able to bio-synthesize copolyesters with 4HHp as a component starting from 4-hydroxyheptanoic acid as the carbon source; however, none of the wild type strains, which were tested, was capable in this regard.

Here also, the detection of 4HHp took place gas chromatographically after methanolysis both in lyophilized cells and also using isolated and purified polyesters.

The inventors have also found that a recombinant strain, which contains the gene of the PHF synthase from *Thiocapsa pfennigii* e.g. a PHF-free mutant GPp104 of *Pseudomonas putida*, can synthesize a new copolyester that contains the 4-hydroxyoctanoic acid component (4HO).

The detection of 4HO took place gas chromatographically after methanolysis both in lyophilized cells and also using isolated and purified polyesters.

The preparation of 4-hydroxyoctanoic acid takes place via the hydrolysis of γ-lactone with NaOH.

Typically, the bacterial cells accumulated the synthesized copolyester up to a concentration of approximately 20% by weight of the dry mass of the cells. The polymer contained, for example: approximately 75 mol% of 3-hydroxybutyric acid, approximately 22 mol% of 3-hydroxyhexanoic acid, approximately 1.5 mol% of 4-hydroxyoctanoic acid and approximately 3 mol% of 3-hydroxy-octanoic acid.

In this regard also, numerous wild types of strains were also examined in regard to their capacity for big-synthesizing copolyesters with 4HO as a subunit starting from 4-hydroxy-octanoic acid as the carbon source; however, none of the tested wild strains were capable of this.

The new copolyesters, that are prepared by means of the process in accordance with the invention also exhibit thermoplastic properties and they can be processed in a problem-free manner using the techniques which are conventional in plastics technology.

These were water-insoluble thermoplastic copolymer that have a high degree of bio-compatibility which makes these materials appear to be usable for application in medical technology—e.g. as implants—or as suture material or similar articles.

Basically, the dine of cultivation of the microorganisms, which are used for the purposes of the present invention, is governed by the culture conditions which are governed primarily by the temperature, the oxygen content of the medium (aerobic conditions) and by the medium itself, the quantity of the carbon source, the mineral salts, the trace elements and/or the pH value. The quantity of the substrates used in each case is governed by the microorganism in question. However, one can start from concentrations in the range from approximately 0.1% (weight/volume) up to 10% (weight/volume) corresponding to 100 g/L or, especially, 0.2% (weight/volume) up to 5 (weight/volume).

The harvesting of the cells can generally take place during the log phase up to the stationary phase; it should preferably take place in the stationary phase. The bacterial cells can be obtained from the medium in their entirety either after single culturing (batch process or fed-batch process) or they can be obtained continuously via continuous culturing, e.g. by means of conventional centrifugation or filtration processes.

After optionally washing, for example with a buffer, preferably a phosphate buffer or, especially preferably, a sodium phosphate buffer in the neutral region of approximately pH 7.0, the harvested cells can be frozen, lyophilized or treated by means of spray drying.

Obtaining the polyesters in accordance with the invention can take place in accordance with known methods; dissolution or extraction is preferably carried out with organic solvents, especially by means of halogenated or, preferably, chlorinated hydrocarbons or, especially preferably, by means of chloroform or methylene chloride.

The copolyester, that are obtained in accordance with the invention, are easy to process in the form of thermoplastics and are usable in many ways. For example, in surgery, for articles for closing wounds, e.g. as suture material or clamps or similar articles, as an attachment element for bones, e.g. fixation pins, plates, screws, dowels, as a separating material, filling material or covering material, e.g. in the form of fabric, fleece or wadding. Likewise, the polyesters in accordance with the invention can be used in pharmaceutical galenic preparations, e.g. in the form of ancillary substances, carrier materials, release systems for medicinal agents or for the encapsulation and/or micro-encapsulation of substances and active materials.

In addition, the preparation of biodegradable packaging materials such as foils, bottles, ampoules, cans, pouches, boxes, cases or similar items is also possible by means of the present invention.

The recombinant bacteria, which are to be pre-cultivated in a complex medium have the advantage that, as a result of this, intense multiplication of the biomass is achieved initially in order then to stimulate the bacteria biochemically to bio-synthesize the desired PHF.

An additional carbon source which promotes growth, selected from the group comprising: citric acid, octanoic acid and gluconic acid; their salts, esters and lactones; hexoses, especially glucose and fructose; as well as their mixtures which is to be added to the nutrient medium for the culturing of the bacteria has the advantage that, as a result of this, venous subunits can be incorporated on the one hand and, on the other hand, the bacteria grow considerably faster in part and, at the same time, they bio-synthesize a larger quantity of the desired PHF.

The procedures carried out in the form of a batch process, a fed-batch process, a two-step process or a continuous flow process have the advantage that the process of the present invention can be carried out using processes that are conventional in large scale industrial biotechnology.

The procedures wherein the poly(hydroxy fatty acid) is obtained in a concentration of approximately 15 to 70% by weight or, especially approximately 15 to 50% by weight or, preferably, approximately 40% by weight based on the dry mass of the bacterial cells have the advantage that an economical ratio of the polyester yield to the dry mass of the bacterial cells can be obtained so that, seen economically, the yield obtained is profitable.

Profitability calculations have shown that the lower limit for profitability can lie in the order of approximately 30% by weight of polyester based on the dry mass of the bacterial cells.

However, using the present invention, it is possible to achieve values which are distinctly in excess of 40% PHF based on the dry mass of the bacterial cells.

In this way, the yield can, of course, be increased considerably further by suitable alteration of the biochemical and/or biophysical parameters in order to control the biotechnological process, e.g. pH adjustment, pressure and/or temperature adjustment step-wise addition of the substrates and/or the substrate mixtures, cell densities, nutrient medium compositions, etc.

The procedures wherein the poly(hydroxy fatty acids) are obtained in the form of copolyesters with at least two or, preferably, three subunits have the advantage that, in the case of copolyesters with at least two subunits, the chemical, biochemical and physical properties of the polyester can be adjusted by varying the different subunits in fine steps if one offers the appropriate substrates to the bacteria.

Allowing the recombinant bacteria to grow to cell densities of up to 100 g of cellular dry mass per liter of bacterial nutrient medium has the advantage that, together with appropriate dimensions for large scale industrial plants, relatively small volumes contain a considerable biomass and thus increase the productivity significantly relative to lower cell densities.

To offer the substrate carbon source in an excess quantity, or at a concentration of approximately 0.1 to 5% by weight has the advantage that the substrate is then taken up preferentially by the bacteria because of the concentration gradient and is then used for the production of the polyester.

The procedures wherein one increases the concentration of the substrate carbon source in the culture medium in steps, optionally with pre-cultivation in the presence of an additional carbon source which does not save as a substrate have the advantage that, as a result of the step-wise increase in the concentration of the substrate carbon source, the total process can be controlled better in the direction of higher yields.

Procedures in which one adds approximately 0.5% (weight/volume) of neutralized substrate carbon source after approximately 12 h and 24 h at approximately 27° C. to 35° C. or, preferably, at approximately 30° C.; in which cultivation takes place for approximately 24 h to 96 h or, especially, for approximately 36 h to 72 h or, preferably, for approximately 48 h to 72 h; or in which the recombinant bacteria are cultivated under conditions of deficiency, preferably under conditions of a deficiency of nitrogen, magnesium or phosphate give advantageous process conditions for the biotechnological preparation of PHF in accordance with the present invention.

Processes in which the harvested recombinant bacteria are broken open by means of physical and/or chemical and/or biochemical processes in order to obtain the poly(hydroxy fatty acids) that have been produced bio-technically; or in which the harvested recombinant bacteria are lyophilized and then extracted with an organic solvent, preferably chloroform or methylene chloride, in order to break open the recombinant bacteria and to obtain the poly(hydroxy fatty acids) have the advantages that all the usual methods in biotechnology for breaking open bacteria can be used in order to obtain the bio-industrially produced PHF.

Since these are generally heavier than the nutrient medium and the cell debris that surround them, the PHF can easily be separated and obtained by accelerated sedimentation, for example by centrifugation.

Processes in which the extracted poly(hydroxy fatty acid) product is precipitated by introducing a hydrophilic solvent, especially water or a lower alcohol, preferably ethanol, and the product is obtained in essentially pure form by removing the hydrophilic solvent have the advantage that, as a result of the introduction of a PHF product, that has been dissolved by means of an organic solvent, in water or a lower alcohol, preferably ethanol, the PHF are precipitated and a purification step is consequently achieved which can be compared with a recrystallization process in organic chemistry for the purification of the desired product.

To use an enzyme cocktail in processes in which harvested recombinant bacteria are broken open by means of detergents and/or a lytic enzyme cocktail as a result of which the bacterial cell grana, which contain the poly(hydroxy fatty acid), sediment to the bottom of the big-reactor and are collected from there in order to be processed further; or in which the lytic enzyme cocktail contains enzymes which are selected from the group which comprises: lysozyme; proteases; other hydrolytic enzymes; as well as their mixtures has the advantage that here, specifically, the bacterial cell wall and the membrane are destroyed enzymatically so that the grana, which contain the PHF, are precipitated from the cytoplasm and sediment on the bottom of the reactor. Since, especially preferably, proteolytic and lytic enzymes, e.g. lysozymes or even lipases, are used as a rule in this regard, the entire biotechnological preparation essentially comprises macromolecules—namely the desired polyester which is being synthesized—as well as a plurality of smaller molecules which arise as a result of the enzymatic cleavage of the nucleic acids, proteins glycoproteins, polysaccharides and lipids, that are contained in the cells and the cell walls and cell membrane, and which can thus be separated from one another with case without the isolated PHF containing significant impurities from other bacterial compounds.

The use of detergents is especially advantageous in this connection since proteins and nucleic acids are also solubilized, in particular, as a result of this and they are then degraded in the form of quasi colloid particles which are suspended in the aqueous solutions of the other enzymes.

In this connection, note must of course be taken of the fact that detergents are applied in which the enzymes that are used are still very active or are very active for the first time. Such a mild detergent is, for example, octyl glucoside. On the over hand, it is known, for example in regard to the V8 protease from *Staphylococcus aureus*, that it still reveals intense proteolytic activity in 1 to 2% sodium dodecyl sulfate.

Bacterial strains *Pseudomonas putida* GPp104 (pHP1014::B28+) [DSM #9417] and *Alcaligenes eutrophus* PHB 4 (pHP1014::B28+) [DSM #9418], preferably containing and expressing a minimally small DNA fragment with the gene of the poly(hydroxy fatty acid) synthase from

*Thiocapsa pfennigii*, and more preferably that it is capable of transforming at least one substrate carbon source into a poly(hydroxy fatty acid) with at least one subunit and storing this in an intracellular manner, whereby the substrate carbon source is selected from the group which comprises: levulinic acid, salts of levulinic acid, esters of levulinic acid, lactones of levulinic acid, substituted levulinic acid or, as the case may be, its derivatives; 5-hydroxyhexanoic acid, its salts, esters and lactones; 4-hydroxyheptanoic acid, its salts, esters and lactones; 4-hydroxyoctanoic acid, its salts, esters and lactones; their halogenated derivatives as well as their mixtures; relate to new recombinant bacterial strains in accordance with the invention which contain and express the genes phaC and phaE from *Thiocapsa pfennigii* which are relevant for PHF synthesis.

The BamHI fragment B28, that is contained in the newly constructed bacterial strains in accordance with the invention, was obtained following BamHI digestion of the EcoRI fragment E156 and essentially comprises the two genes phaC and phaE.

The bacterial strains in accordance with the invention and selected from the group which comprises *Pseudomonas putida* GPp104 (pHP1014::B28+) [DSM #9417] and *Alcaligenes eutrophus* PHB 4 (pHP1014::B28+) [DSM #9418] generate especially high yields of PHF.

PHF in the form in which it is obtainable in accordance with a process according to one of the described processes; in particular, the following PHF or, as the case may be, polyesters or, as the case may be, copolyesters could be obtained characterized by the feature that it contains groups of subunits which are selected from the group:

(A) 3-hydroxybutyric acid, 3-hydroxyvaleric acid and 4-hydroxy-valeric acid;

(B) 3- hydroxybutyric acid, 3-hydroxyvaleric acid, 4-hydroxy-valeric acid, 3-hydroxyhexanoic acid and 3-hydroxyoctanoic acid;

(C) 3-hydroxybutyric acid, 3-hydroxyhexanoic acid, 5-hydroxy-hexanoic acid and 3-hydroxyoctanoic acid;

(D) 3-hydroxybutyric acid, 3-hydroxyvaleric acid, 3-hydroxy-hexanoic acid, 3-hydroxyheptanoic acid, 4-hydroxyheptanoic acid and 3-hydroxyoctanoic acid;

(E) 3-hydroxybutyric acid, 3-hydroxyhexanoic acid, 3-hydroxy-octanoic acid and 4-hydroxyoctanoic acid;

(F) 3-hydroxybutyric acid, 3-hydroxyhexanoic acid and 5-hydroxy-hexanoic acid;

(G) 3-hydroxybutyric acid, 3-hydroxyvaleric acid, 3-hydroxy-heptanoic acid and 4-hydroxyheptanoic acid;

(H) 3-hydroxybutyric acid, 3-hydroxyvaleric acid, 3-hydroxy-hexanoic acid, 3-hydroxyoctanoic acid and 4-hydroxyoctanoic acid;

(I) 3-hydroxybutyric acid, 3-hydroxyhexanoic acid and 4-hydroxy-hexanoic acid;

(J) 3-hydroxybutyric acid and 5-hydroxyhexanoic acid.

Poly(hydroxy fatty acid) may be characterized by the feature that the to poly(hydroxy fatty acid) with the subgroup unit (A) has the following quantitative composition: approximately 35 mol% to 65 mol% of 3-hydroxybutyric acid; approximately 30 mol% to 50 mol% of 3-hydroxyvaleric acid; and approximately 5 mol% to 20 mol% of 4-hydroxyvaleric acid. The poly(hydroxy fatty acid) may be characterized by the feature that the poly (hydroxy fatty acid) with the subgroup unit (B) has the following quantitative composition: approximately 10 mol% to 15 mol% of 3-hydroxybutyric acid; approximately 40 mol% to 60 mol% of 3-hydroxyvaleric acid; approximately 10 mol% to 20 mol% of 4-hydroxyvaleric acid; approximately 5 mol% to mol% of 3-hydroxyhexanoic acid; and approximately 2 mol% to 10 mol% of 3-hydroxyoctanoic acid. The poly(hydroxy fatty acid) may be characterized by the feature that the poly(hydroxy fatty acid) with the subgroup unit (C) has the following quantitative composition: approximately 60 mol% to 80 mol% of 3-hydroxybutyric acid; approximately 2 mol% to 10 mol% of 3-hydroxyhexanoic acid; approximately 15 mol% to 30 mol% of 5-hydroxyhexanoic acid; and approximately 1 mol% to 5 mol% of 3-hydroxyoctanoic acid. The poly (hydroxy fatty acid) may be characterized by the feature that the poly(hydroxy fatty acid) with the subgroup unit (D) has the following quantitative composition: approximately 30 mol% to 50 mol% of 3-hydroxybutyric acid;

approximately 10 mol% to 30 mol% of 3-hydroxyvaleric acid; approximately 15 mol% to 35 mol% of 3-hydroxyhexanoic acid; approximately 1 mol% to 10 mol% of 3-hydroxyheptanoic acid; approximately 1 mol% to 10 mol% of 4-hydroxyheptanoic acid; and approximately 1 mol% to 10 mol% of 3-hydroxyoctanoic acid. The poly (hydroxy fatty acid) may be characterized by the feature that the poly(hydroxy fatty acid) with the subgroup unit (E) has the following quantitative composition: approximately 65 mol% to 85 mol% of 3-hydroxybutyric acid; approximately 15 mol% to 30 mol% of 3-hydroxyhexanoic acid; approximately 1 mol% to 5 mol% of 3-hydroxyoctanoic acid; and approximately 0.5 mol% to 5 mol% of 4-hydroxyoctanoic acid. The poly(hydroxy fatty acid) may be characterized by the feature that the poly(hydroxy fatty acid) with the subgroup unit (F) has the following quantitative composition: approximately 50 mol% to 80 mol% of 3-hydroxybutyric acid; approximately 3 mol% to 10 mol% of 3-hydroxyhexanoic acid; approximately 10 mol% to 30 mol% of 5-hydroxyhexanoic acid. The poly(hydroxy fatty acid) may be characterized by the feature that the poly (hydroxy fatty acid) with the subgroup unit (G) has the following quantitative composition: approximately 30 mol% to 80 mol% of 3-hydroxybutyric acid; approximately 5 mol% to 20 mol% of 3-hydroxyvaleric acid; approximately 1 mol% to 5 mol% of 3-hydroxyheptanoic acid; and approximately 3 mol% to 10 mol% of 4-hydroxyheptanoic acid. The poly(hydroxy fatty acid) may be characterized by the feature that the poly(hydroxy fatty acid) with the subgroup unit (H) has the following quantitative composition: approximately 70 mol% to 90 mol% of 3-hydroxybutyric acid; approximately 1 mol% to 5 mol% of 3-hydroxyvaleric acid; approximately 10 mol% to 20 mol% of 3-hydroxyhexanoic acid; approximately 1 mol% to 5 mol% of 3-hydroxyoctanoic acid; and approximately 0.5 mol% to 4 mol% of 4-hydroxyoctanoic acid. These preferred quantitative compositions of the PHF in the form in which they are obtained by the process in accordance with the invention. All the PHF that are obtained are capable of being processed as a thermoplastic and exhibit high flexibility.

A DNA fragment which codes for a pha E component and a pha C component of the poly(hydroxy fatty acid) synthase from *Thiocapsa pfennigii* is characterized by the feature that it has at least the nucleotide sequence of sequence sections 180 through 1280 (phaE) and 1322 through 2392 (phac) of the DNA sequence SEQ ID NO:1, obtainable by means of BamHI digestion of a 15.6 kbp EcoRI DNA fragment from *Thiocapsa pfennigii* relates to a DNA fragment which carries the genes phaE arm phaE from *Thiocapsa pfennigii*. The phaC gene codes for the phaC protein and the phaE gene codes for the phaE protein.

The two proteins together exhibit PHF synthase activity.

Further advantages and characteristic features of the present invention arise on the basis of the description of the examples and on the basis of the Figures. The following aspects are shown:

EXAMPLES

Example 1

8 L of mineral salt medium (Schlegel, H. G., Kaltwasser, H. and Gottschalk, G., 1961, *Arch. Microbiol.* 38: 209–222) with the composition

| | |
|---|---|
| $Na_2HPO_4 \times 12H_2O$ | 9.0 g |
| $KH_2PO_4$ | 1.5 g |
| $NH_4Cl$ | 0.5 g |
| $MgSO_4 \times 7H_2O$ | 0.2 g |
| $CaCl_2 \times 2H_2O$ | 0.02 g |
| $Fe(III)NH_4$ citrate | 0.0012 g | whereby the ingredients are dissolved in 1 liter of deionized water which contained 10 mL of a trace element solution with the composition

| | |
|---|---|
| EDTA (Titriplex III) | 500 mg |
| $FeSO_4 \times 7H_2O$ | 200 mg |
| $ZnSO_4 \times 7H_2O$ | 10 mg |
| $MnCl_2 \times 4H_2O$ | 3 mg |
| $H_3BO_3$ | 30 mg |
| $CoCl_2 \times 6H_2O$ | 20 mg |
| $CuCl_2 \times 2H_2O$ | 1 mg |
| $NiCl_2 \times 6H_2O$ | 2 mg |
| $Na_2MoO_4 \times 2H_2O$ | 3 mg | whereby the ingredients are dissolved in one liter of deionized water, supplemented with 0.2% (weight/volume) of neutralized octanoic acid, which had been adjusted to pH 7, was inoculated in an aerated stirred kettle with 500 mL of a stationary pre-culture of the strain *Pseudomonas putida* GPp104 (pHP1014:E156) in a complex medium consisting of beef extract (3 g) and peptone (5 g) dissolved in one liter of deionized water. After 12 and 24 hours of cultivation at 30° C., 0.5% (weight/volume) of neutralized levulinic acid were added in each case. Cell harvesting took place after a total of 48 hours of cultivation.

The analysis of the polymer, that was accumulated by the cells, resulted in a polyester concentration of 15% by weight of the dry mass of the cells. The polymer consisted of approximately 11 mol%, of 3-hydroxybutyric acid, approximately 59 mol% of 3-hydroxyvaleric acid, approximately 15 mol% 4-hydroxyvaleric acid, approximately 10 mol% of 3-hydroxyhexanoic acid and approximately 5 mol% of 3-hydroxyoctanoic acid.

Example 2

The procedure was followed as indicated in Example 1, except that use was made of the strain *Alcaligenes eutrophus* PHB 4 (pHP1014::E156) instead of *Pseudomonas putida* GPp104 (pHP1014::E156) and that, instead of neutralized octanoic acid, 0.3% neutralized gluconic acid was offered as the carbon source in addition to levulinic acid.

The analysis of the polymer, that was accumulated by the cells, resulted in a polyester concentration of 31% by weight of the dry mass of the cells. The polymer consisted of approximately 55 mol% of 3-hydroxybutyric acid, approximately 36 mol% of 3-hydroxyvaleric acid and approximately 9 mol% of 4-hydroxyvaleric acid.

Figure 3:
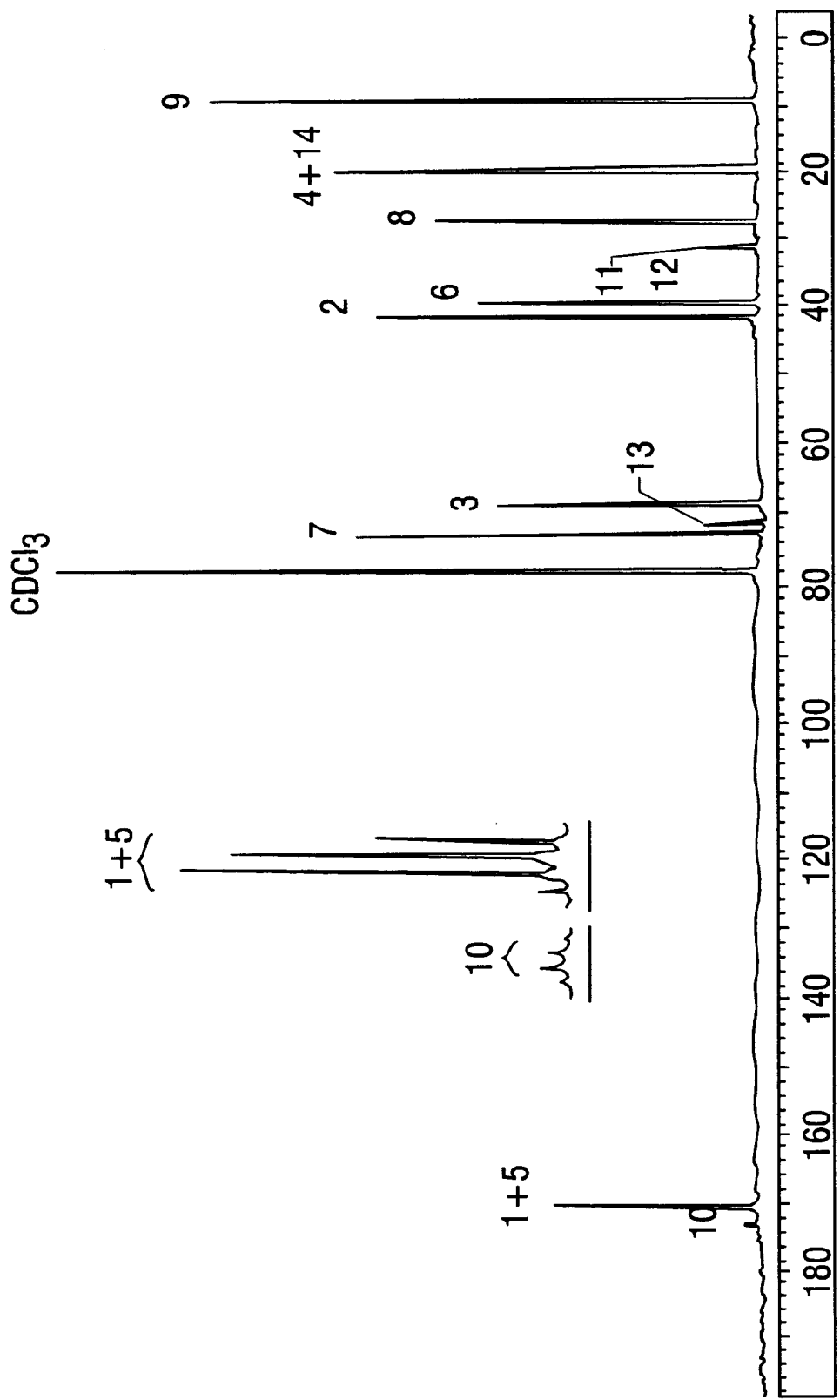
FIG. 3: $^{13}$C-NMR-spectrum of poly(3HB-co-3HV-co-4HV).
Figure 4:
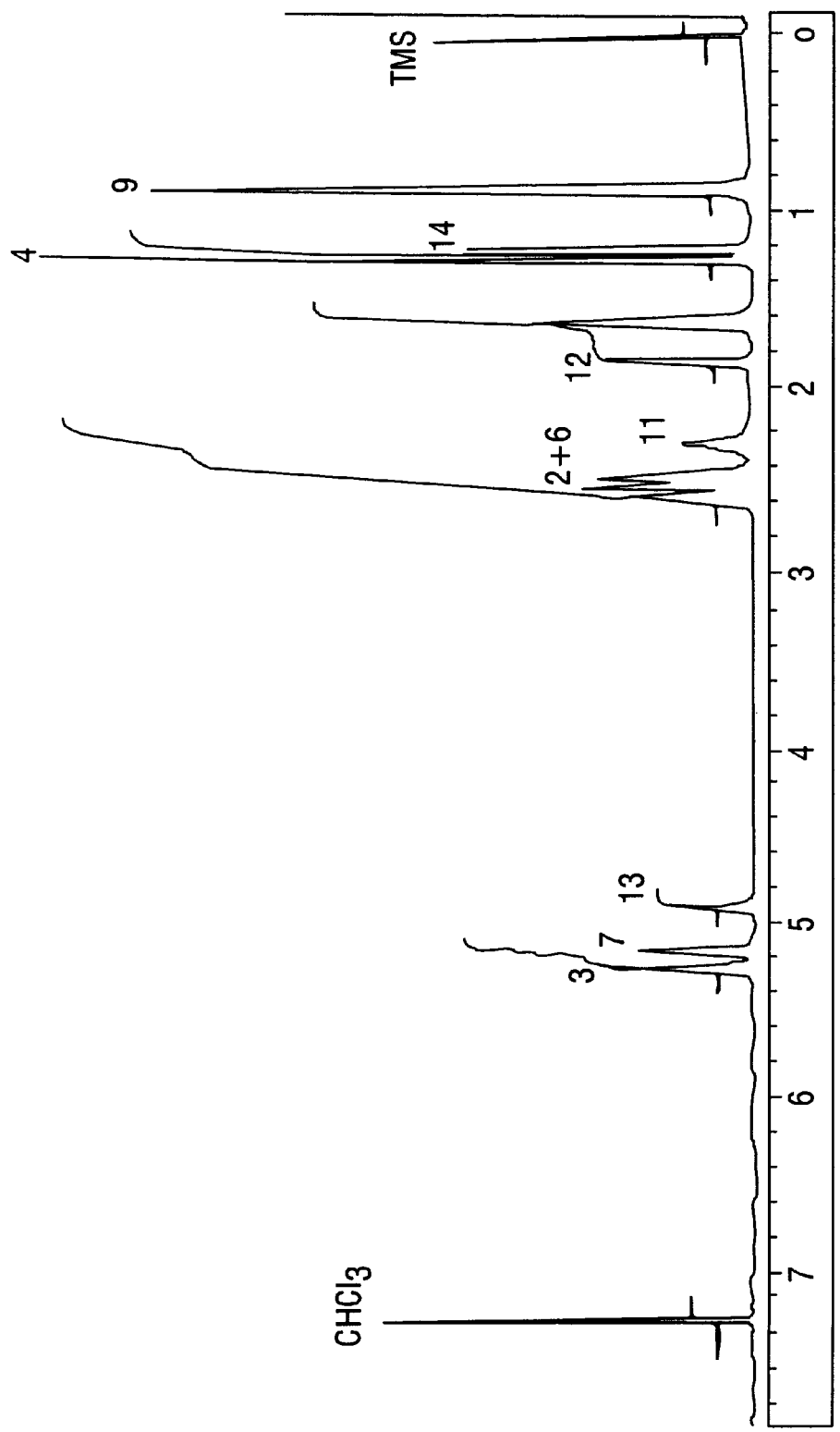
FIG. 4: $^1$H-NMR spectrum of the purified PHF from *A. eutrophus*.
Figure 5:
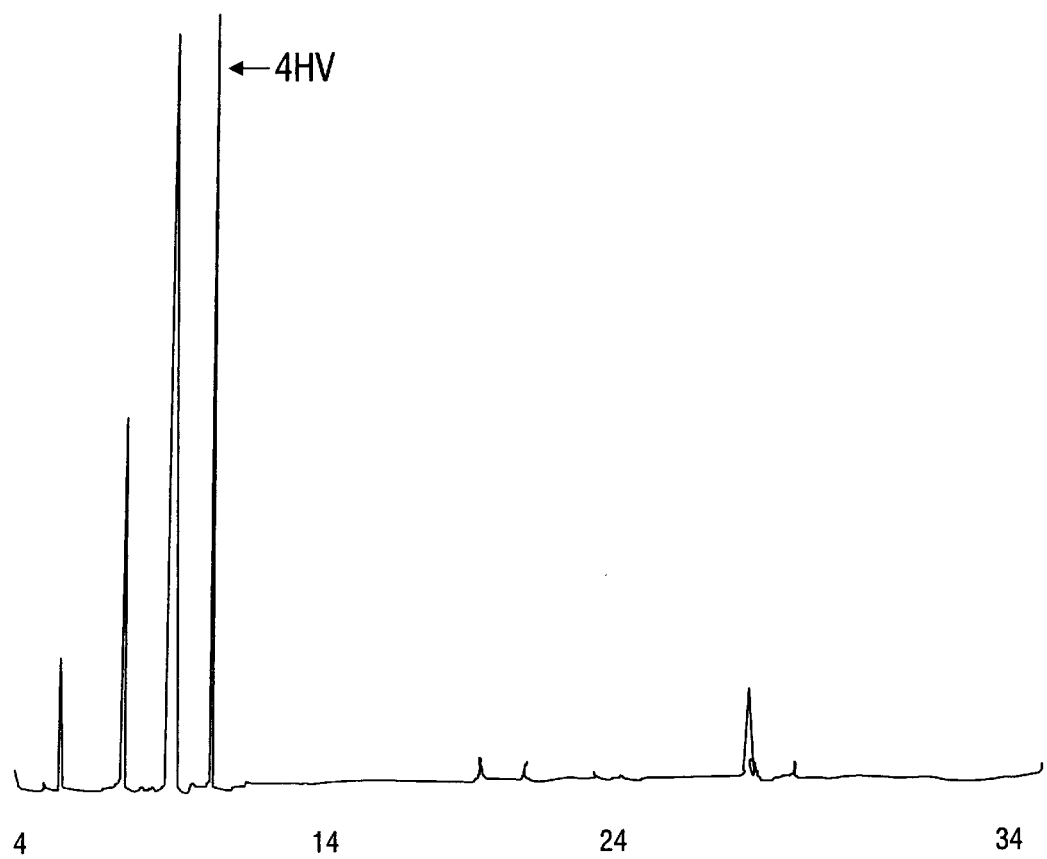
FIG. 5: Gas chromatogram of the purified PHF from *A. eutrophus*.

The polyesters had, for example, the analytical data that are shown in the Figures, whereby FIG. 3 reproduces the $^{13}$C-NMR spectrum and FIG. 4 reproduces the $^1$H-NMR spectrum. The signal assignment is found on the basis of the numbering which is indicated in the structural formula of poly(3HB-co-3HV-co - 4HV), which is shown in FIG. 2. The gas chromatogram after methanolysis of this polyester is shown in FIG. 5.

Example 3

The procedure was followed as indicated in Example 2, except that a third portion of 0.5% (weight/volume) of levulinic acid was added after 36 hours and cultivation took place for a further 24 hours.

The analysis of the polymer, that was accumulated by the cells, resulted in a polyester content of 35% by weight of the dry mass of the cells. The polymer consisted of approximately 43 mol% of 3-hydroxybutyric acid, approximately 45 mol% of 3-hydroxyvaleric acid and approximately 12 mol% of 4-hydroxyvaleric acid.

Example 4

The procedure was followed as indicated in Example 2, except that the volume of the inoculum from the pre-culture amounted to only 3 mL and that, as the main culture, inoculation took place with 50 mL of the aforementioned mineral salt medium in a 500 mL erlenmeyer flask. The flasks were then shaken aerobically for 72 hours before cell harvesting took place.

The analysis of the polymer, that was accumulated by the cells, resulted in a polyester content of approximately 25% by weight of the dry mass of the cells. The polymer consisted of approximately 61 mol% of 3-hydroxybutyric acid, approximately 32 mol% of 3-hydroxyvaleric acid and approximately 7 mol% of 4-hydroxyvaleric acid.

Example 5

Cells of *Alcaligenes eutrophus* PHB-4 (pHP1014::E156) from 50 mL of an aerobic pre-culture, that was 15 hours old, in the complex medium, that was designated in Example 1, were harvested by centrifugation, washed with sterile 0.9% sodium chloride solution and transferred to 50 mL of a modified mineral medium (as described in Example 1, but without $NH_4Cl$), which contained 1% (weight/volume) of levulinic acid and were shaken aerobically for 72 hours.

The analysis of the polymer, that was accumulated by the cells, resulted in a polyester content of approximately 37% by weight of the dry mass of the cells. The polymer consisted of approximately 37 mol% of 3-hydroxybutyric acid, approximately 50 mol% of 3-hydroxyvaleric acid and approximately 13 mol% of 4-hydroxyvaleric acid.

Example 6

8 L of a mineral salt medium (Schlegel et al., 1961) with the composition

| | |
|---|---|
| $Na_2HPO_4 \times 12H_2O$ | 9.0 g |
| $KH_2PO_4$ | 1.5 g |
| $NH_4Cl$ | 0.5 g |
| $MgSO_4 \times 7H_2O$ | 0.2 g |
| $CaCl_2 \times 2H_2O$ | 0.02 g |
| $Fe(III)NH_4$ citrate | 0.0012 g | which had been dissolved in one liter of deionized water which contained 10 mL of a trace element solution with the composition

| | |
|---|---|
| EDTA (Titriplex III) | 500 mg |
| $FeSO_4 \times 7H_2O$ | 200 mg |
| $ZnSO_4 \times 7H_2O$ | 10 mg |
| $MnCl_2 \times 4H_2O$ | 3 mg |
| $H_3BO_3$ | 30 mg |
| $CoCl_2 \times 6H_2O$ | 20 mg |
| $CuCl_2 \times 2H_2O$ | 1 mg |
| $NiCl_2 \times 6H_2O$ | 2 mg |
| $Na_2MoO_4 \times 2H_2O$ | 3 mg | which had been dissolved in one liter of deionized water which was supplemented with 0.3% (weight/volume) of neutralized octanoic acid plus 0.1% (weight/volume) of neutralized precursor substrate and adjusted to pH 7, was inoculated with 500 mL of a stationary pre-culture of the strain *Pseudomonas putida*, GPp104 (pHP1014::E156) in a complex medium consisting of beef extract (3 g) and peptone (5 g) dissolved in one liter of deionized water. After 12 and 36 hours in each case, 0.5% of precursor substrate was re-fed in and harvesting took place after a further 36 hours. The fermentation reactor was stirred at 500 rpm during cultivation and it was aerated at the rate of 800 mL of air per minute.

1. Incorporation of 5-hydroxyhexanoic acid

It was found that a recombinant strain of the PHI:-free mutant GPp104 of *Pseudomonas putida*, which contains and expresses the gene of the PHF synthase from *Thiocapsa pfennigii* can synthesize a copolyester that contains the new component 5-hydroxyhexanoic acid.

After methanolysis, the detection of 5HHx as a component took place gas chromatographically both in lyophilized cells and in the isolated and purified polyester. The isolated and purified polyester was subjected to $^{13}$C-NMR and $^1$H-NMR analysis and the incorporation of 5HHx was confirmed as a result of this.

The preparation of 5-hydroxyhexanoic acid took place starting from 4-acetylacetic acid which had been quantitatively reduced using $NaBH_4$.

The analysis of the polymer, that was accumulated by the cells, resulted in a polyester content of approximately 36% by weight of the dry mass of the cells. The polymer consisted of approximately 71 mol% of 3-hydroxybutyric acid, approximately 4 mol% of 3-hydroxyhexanoic acid and approximately 23 mol% of 5-hydroxyhexanoic and approximately 2 mol% of 3-hydroxyoctanoic acid (and, in addition, a minimal quantity of 4-hydroxyoctanoic acid).

Figure 6:
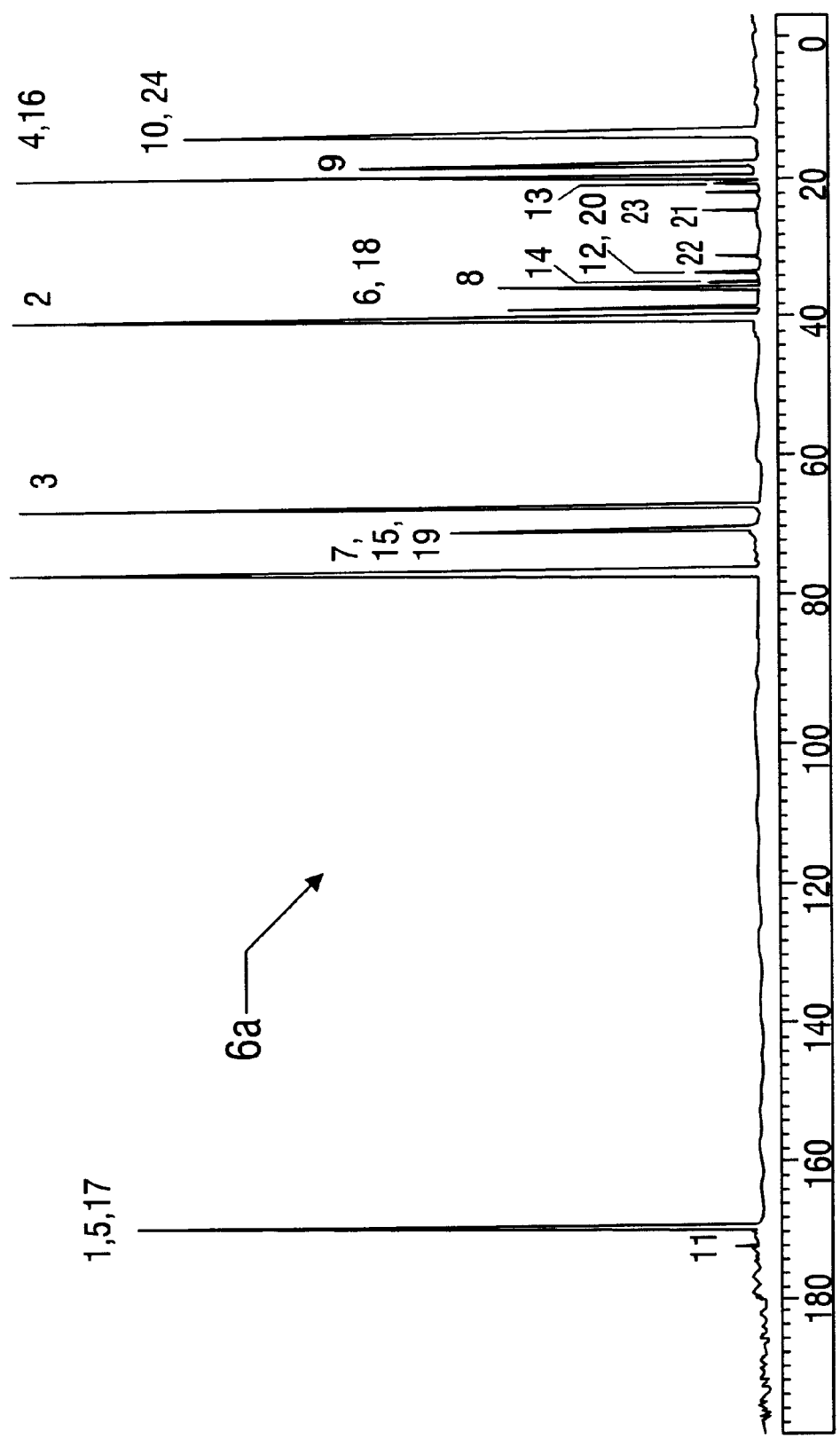
FIG. 6: $^{13}$C-NMR-spectrum of poly(3HB-co-3HHx-co-5HHx-3HO).
Figure 7:
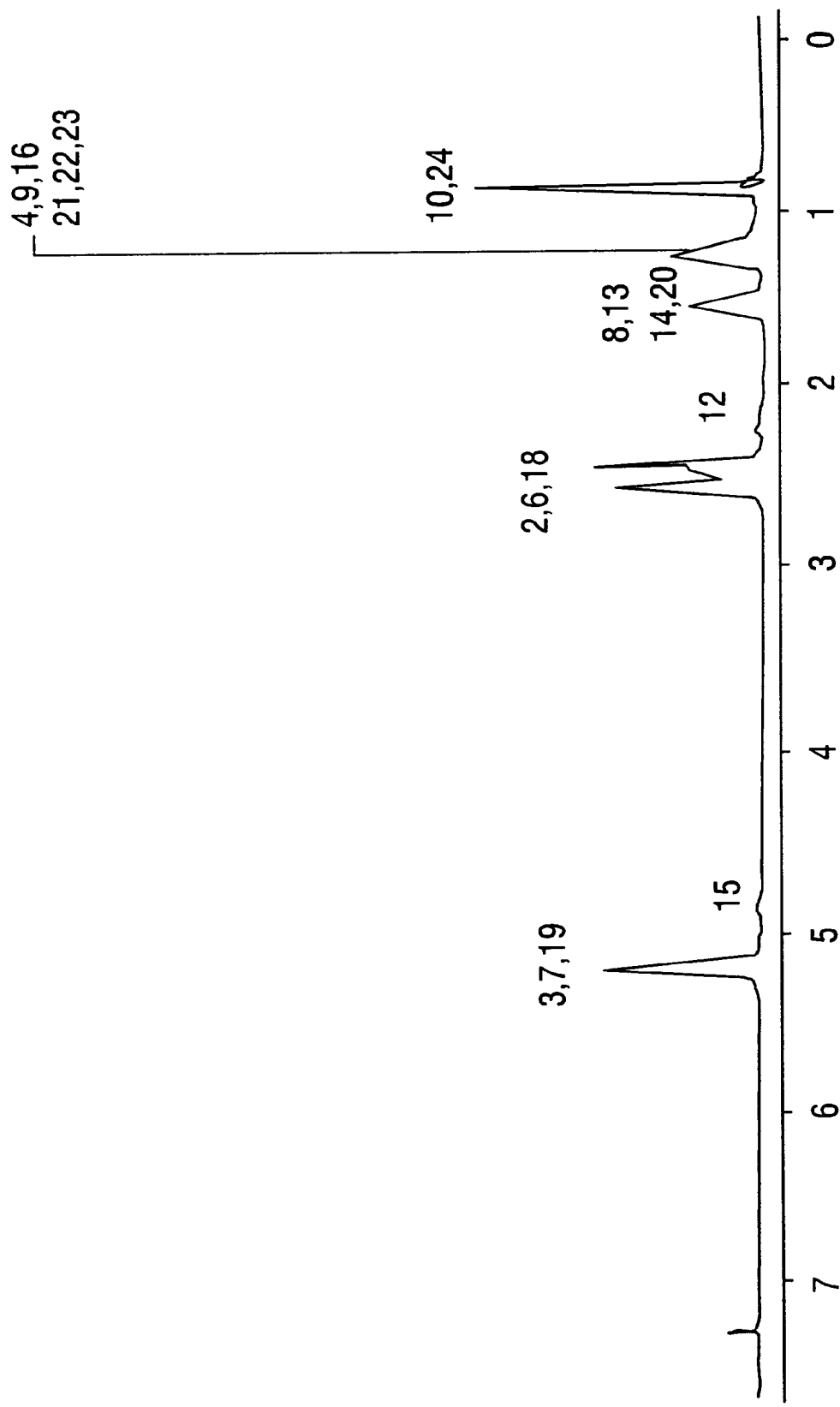
FIG. 7: $^1$H -NMR-spectrum of poly(3HB-co-3HHx-co-5HHx-3HO).
Figure 8:
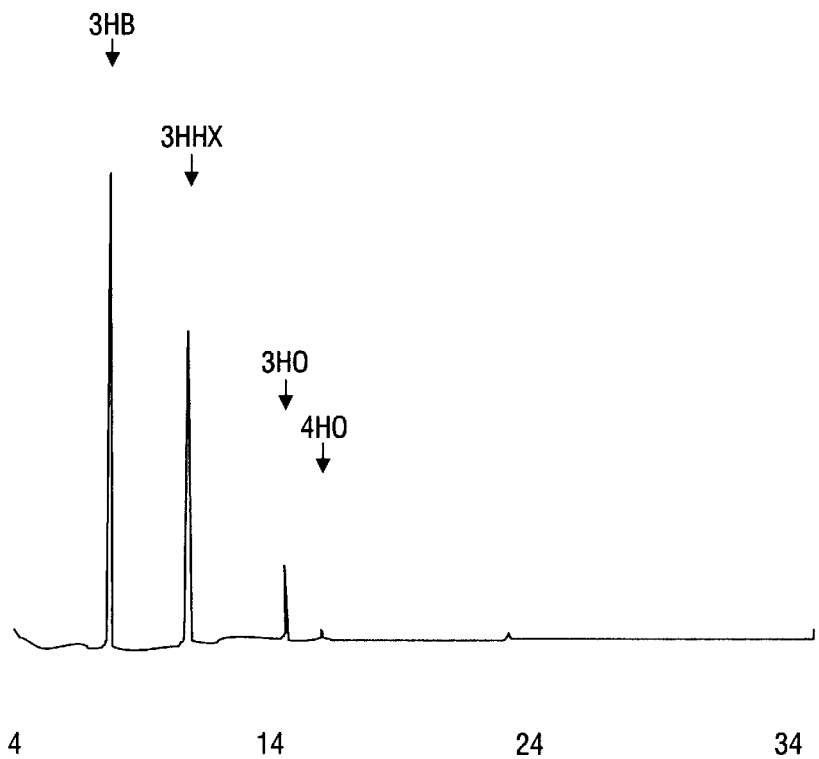
FIG. 8: Gas chromatogram of poly(3HB-co-3HHx-co-5HHx-3HO) after methanolysis.

The polyesters exhibit, for example, the analytical data that are shown in the Figures, whereby FIG. 6 reproduces the $^{13}$C-NMR spectrum and FIG. 7 reproduces the $^1$H-NMR spectrum. The signal assignment is found on the basis of the numbering which is indicated in the structure formula of poly(3HB-co-3HHx-co-5HHx-3HO) which is shown in FIG. 6. The GC analysis after methanolysis is shown in FIG. 8.

Figure 9:
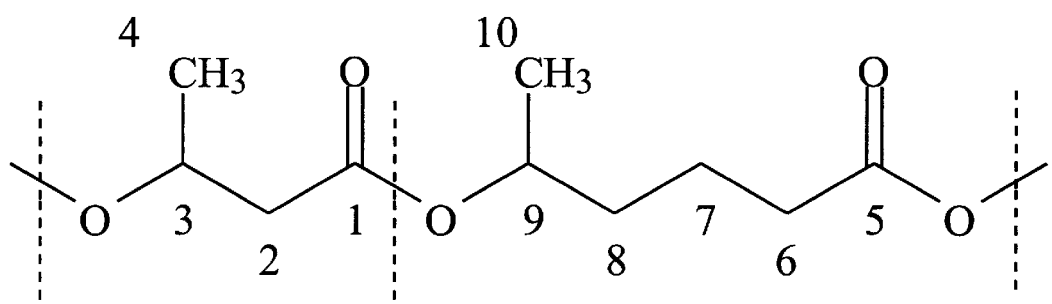
FIG. 9: Structural formula of poly(3-hydroxybutyric acid-co-5-hydroxy-hexanoic acid) [poly(3HB-co-5HHx)].
Figure 10:
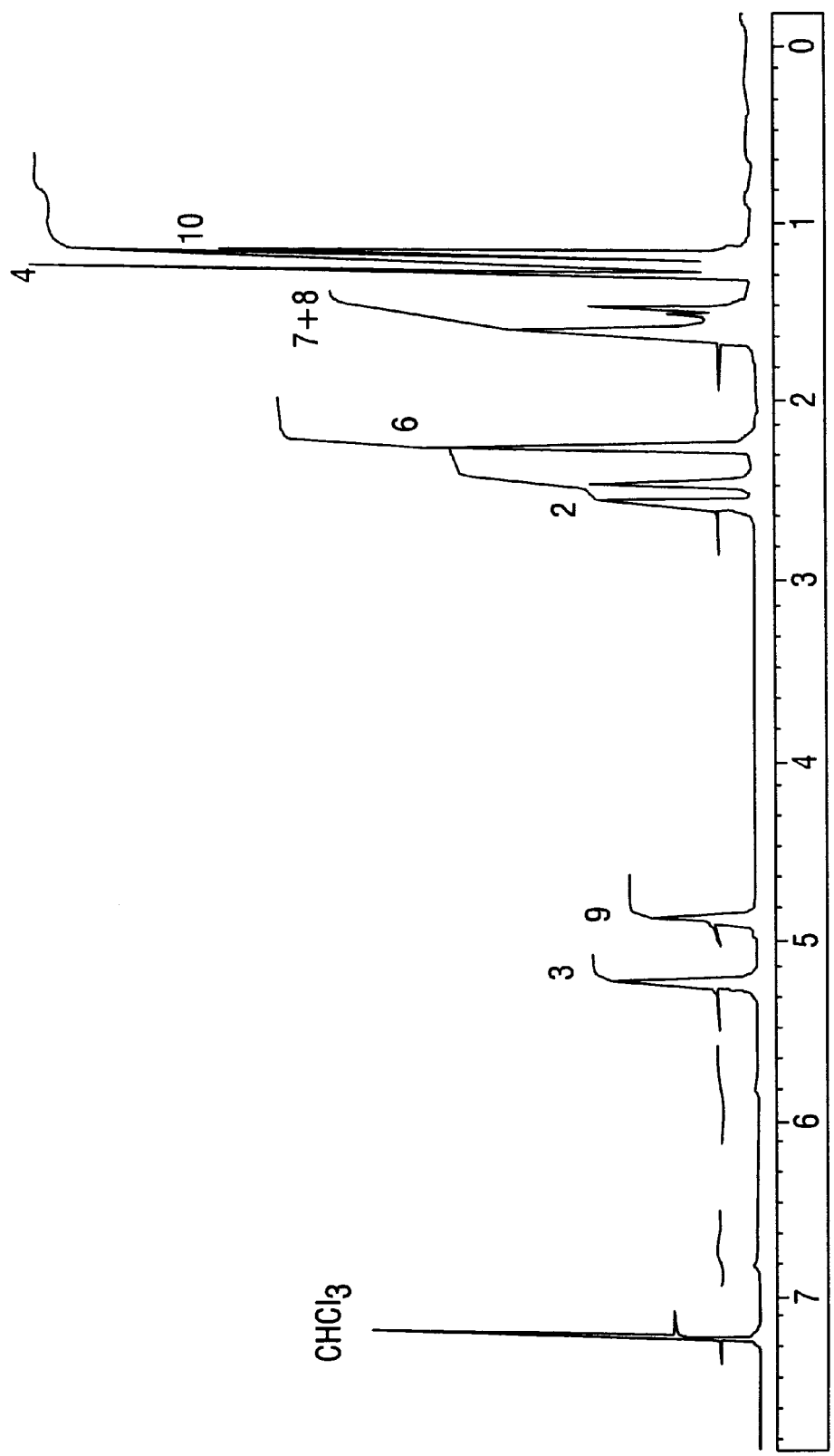
FIG. 10: 13C-NMR-spectrum of poly(3HB-co-5HHx).
Figure 11:
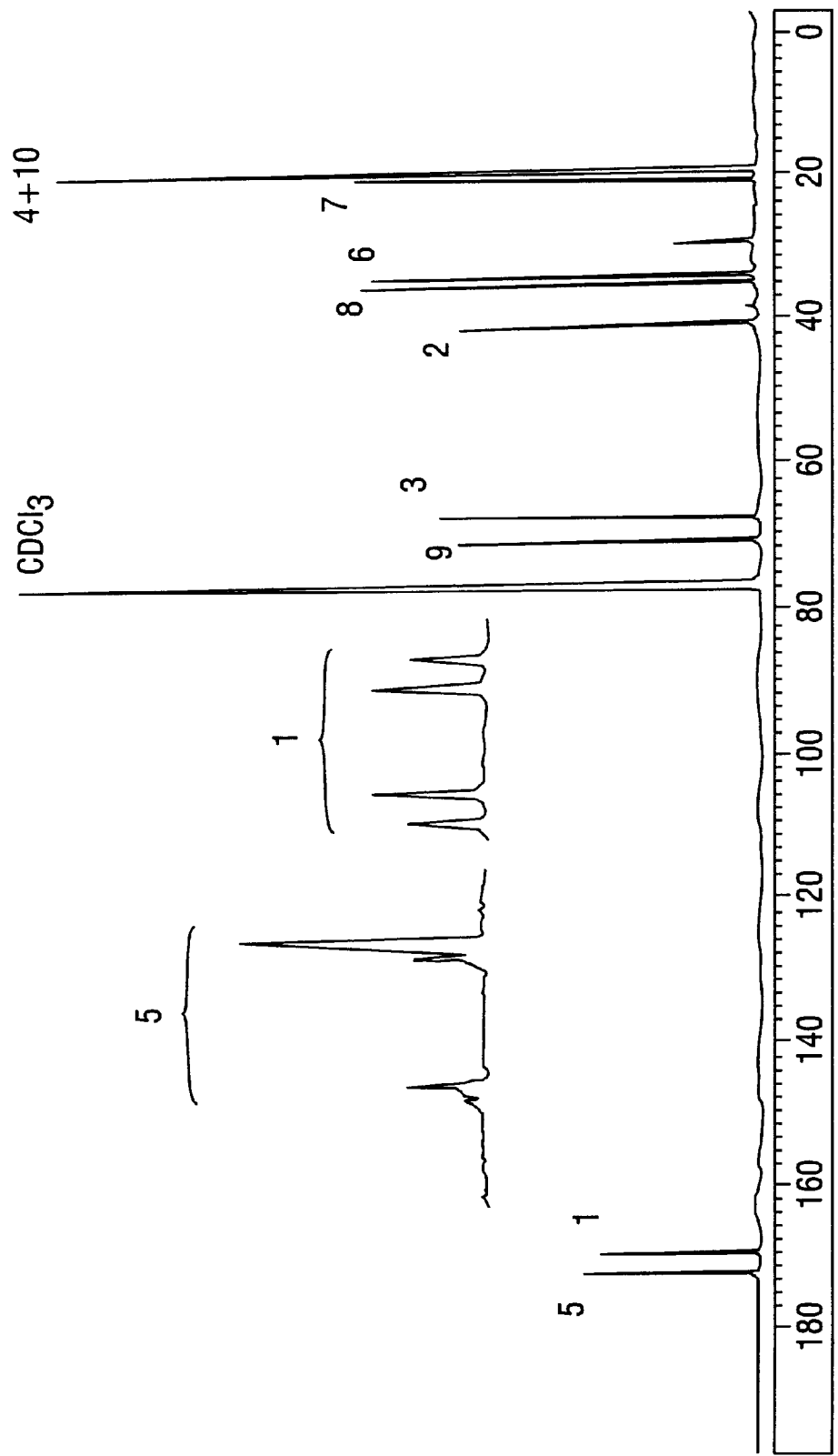
FIG. 11: $^1$H-NMR-spectrum of poly(3HB-co-5HHx).
Figure 12:
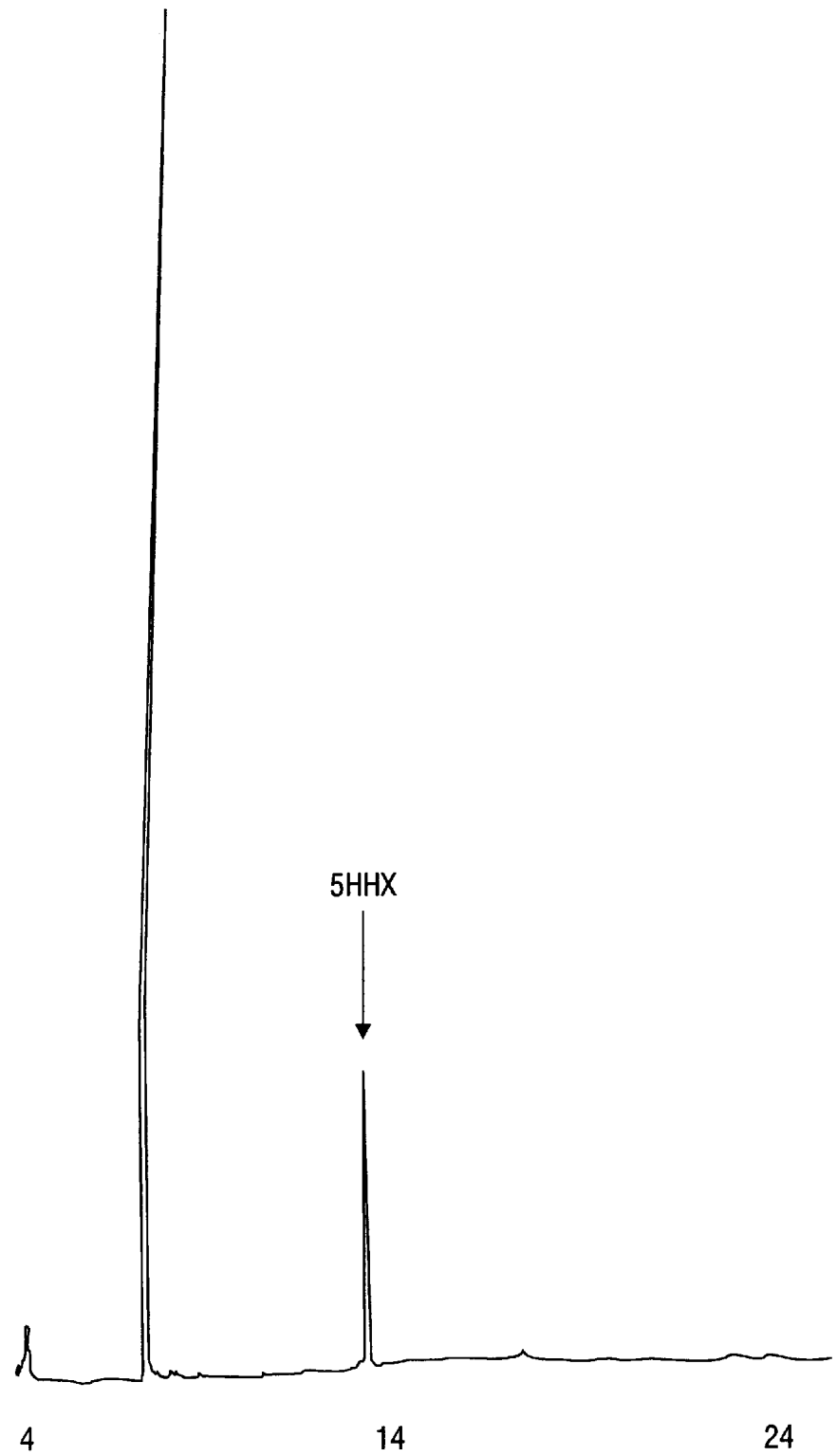
FIG. 12: Gas chromatogram of poly(3HB-co-5HHx).

However, it is also possible to obtain a poly(3HB-co-5HHx) PHF whose spectroscopic and GC data (FIG. 12) are shown in the Figures. The polyesters exhibit, for example, the analytical data that are shown in the Figures, whereby FIG. 10 reproduces the $^{13}$C-NMR spectrum and FIG. 11 reproduces the $^1$H-NMR spectrum. The signal assignment is found on the basis of the numbering which is indicated in the structural formula of poly(3HB-co-5HHx) which is shown in FIG. 9.

2. Incorporation of 4-hydroxyheptanoic acid

It was found that a recombinant strain of the PHF-free mutant GPp104 of *Pseudomonas putida* which contained and expressed the gene of the PHF synthase from *Thiocapsa pfennigii* can synthesize a copolyester that contains the new component 4-hydroxyheptanoic acid (4HHp). After methanolysis, the detection of 4HHp took place gas chromatographically both in lyophilized cells and also in the isolated and purified polyester.

The preparation of 4-hydroxyheptanoic acid took place via hydrolysis of γ-heptolactone with NaOH.

The analysis of the polymer, that was accumulated by the cells, resulted in a polyester content of 39% by weight of the dry mass of the cells. The polymer consisted of 43 mol% of 3-hydroxy-butyric acid, 16 mol% of 3-hydroxyvaleric acid, 27 mol% of 3-hydroxyhexanoic acid, 5 mol% of 3-hydroxyheptanoic acid, 6 mol% of 4-hydroxyheptanoic acid and 3-hydroxyoctanoic acid.

3. Incorporation of 4-hydroxvoctanoic acid

It was found that a recombinant strain of the PHF-free mutant GPp104 of *Pseudomonas pulida* which contained and expressed the gene of the PHF synthase from *Thiocapsa pfennigii*, can synthesize a copolyester that contains the new component 4-hydroxyoctanoic acid (4HHp).

After methanolysis, the detection of 4HO gas took place chromatographically both in lyophilize cells and also in the isolated and purified polyester. Because of the small proportion of 4HO, NMR spectroscopic investigations were not possible.

The preparation of 4-hydroxyoctanoic acid took place via hydrolysis of γ-octalactone with NaOH.

The analysis of the polymer, that was accumulated by the cells, resulted in a polyester content approximately 18% by weight of die dry mass of the cells. The polymer consisted of approximately 75 mol% of approximately 3-hydroxybutyric acid, approximately 22 mol% of 3-hydroxyhexanoic acid, approximately 1.5 mol% of 3-hydroxyoctanoic acid and approximately 3 mol% of 4-hydroxyoctanoic acid.

Example 7

In order to obtain the new polyesters on a smaller scale, e.g. for analytical and test purposes or in order to test strains in terms of their capacity for being able to bio-synthesize these new polyesters, one generally proceeded as follows:

Cells of *Pseudomonas putida* GPp104 (pHP1014::E156) from 50 mL of an aerobic pre-culture, that was 15 hours old, in the complex medium, that was designated in Example 1, were harvested by centrifugation, washed with sterile 0.9% sodium chloride solution and transferred to 50 mL of a modified mineral medium (as described in Example 1, but without $NH_4Cl$) and shaken aerobically for 72 hours.

Using 5-hydroxyhexanoic acid, which was added in portions (0.25 plus 0.25 plus 0.5%) to, in total, a concentration of 1%, *P. putida* GPp104 (pHP1014::E156) accumulated PHF up to a proportion of maximally 40% of the dry mass of the cells and comprised approximately 3-hydroxybutyric acid (approximately 50 to 80 mol%), 3-hydroxyhexanoic acid (approximately 3 to 10 mol%) and 5-hydroxyhexanoic acid (approximately 10 to 30 mol%).

Using 4-hydroxyheptanoic acid, which was added in portions (0.25 plus 0.25 plus 0.5%) to, in total, a concentration of 1%, *P. putida* GPp104 (pHP1014::E156) accumulated PHF up to a proportion of maximally 40% of the dry mass of the cells and comprised approximately 3-hydroxybutyric acid (approximately 30 to 80 mol%), 3-hydroxyvaleric acid (approximately 5 to 20 mol%) and 3-hydroxyheptanoic acid (approximately 1 to 5 mol%) and 4-hydroxy-heptanoic acid (approximately 3 to 10 mol%).

Using 4-hydroxyoctanoate, which was fed in four times with a concentration of 0.2%, *P. putida* GPp104 (pHP1014::E156) accumulated PHF up to a proportion of maximally approximately 50% of the dry mass of the cells and comprised 3-hydroxybutyric acid (approximately 70 to 90 mol%), 3-hydroxyvaleric acid (approximately 1 to 5 mol%), 3-hydroxyhexanoic acid (approximately 10 to 20 mol%), 3-hydroxyoctanoic acid (approximately 1 to 5 mol%) and 4-hydroxyoctanoic acid (approximately 0.5 to 4 mol%).

Example 8

In order to obtain the new polyesters on a smaller scale for analytical and/or test purposes or in order to test the strains in terms of their capacity for being able to bio-synthesize these new polyesters, one also proceeded alternatively as follows.

One proceeded as indicated in Example 1, except that the volume of the inoculum from the pre-culture amounted to only 3 mL and that, as the main culture, inoculation was carried out with 50 mL of the aforementioned mineral salt medium in a 500 mL erlenmeyer flask. The flasks were then shaken aerobically for 72 hours before cell harvesting took place.

The results of the accumulation process (proportion of PHF on the dry mass of the cells and the composition of the polymer) were recorded and varied within the framework which is described in Example 7.

Example 9

Analogously to the Examples 1 through 7, the new bacterial strains *Pseudomonas putida* GPp104 (pHP1014::B28+), DSM No. 9417, and *Alcaligenes eutrophus* PHB4 (pHP1014::B28+), DSM No. 9418, were used as the production organisms.

Figure 13:
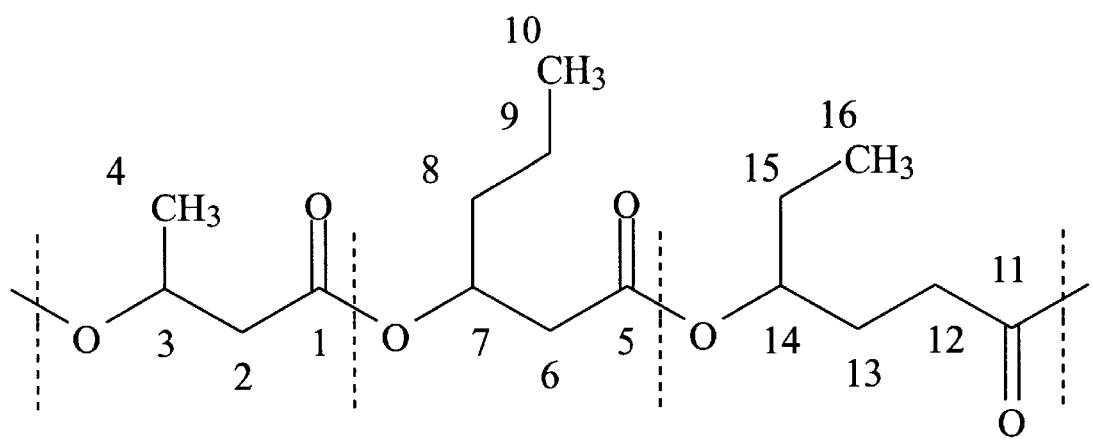
FIG. 13: Structural formula of poly(3-hydroxybutyric acid-co-3-hydroxy-hexanoic acid-co-4 hydroxyhexanoic acid) [poly(3HB-co-3HHx-co-4HHx)].
Figure 14:
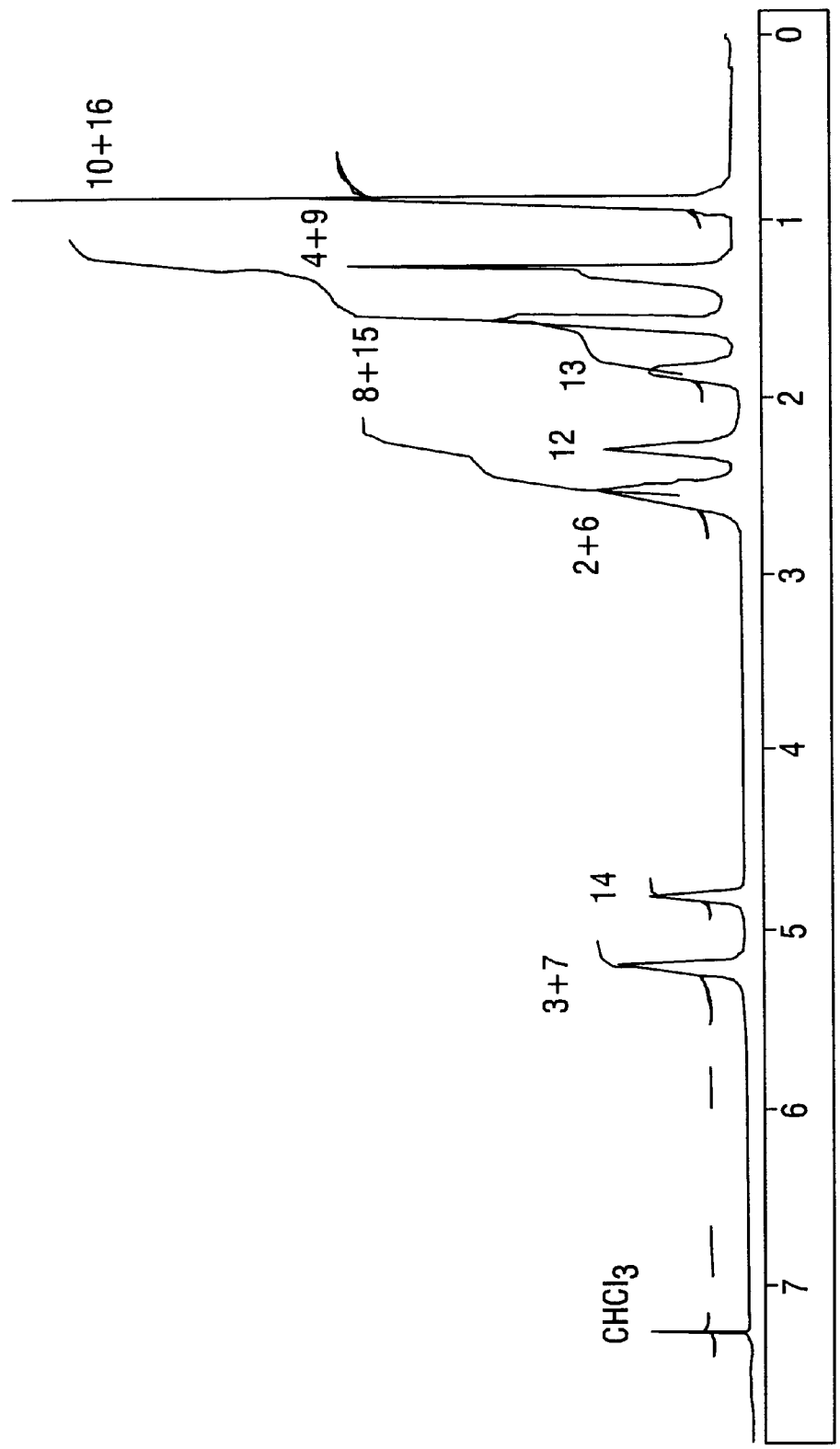
FIG. 14: 13C-NMR-spectrum of poly(3HIB-co-3HHx-co-4HHx).
Figure 15:
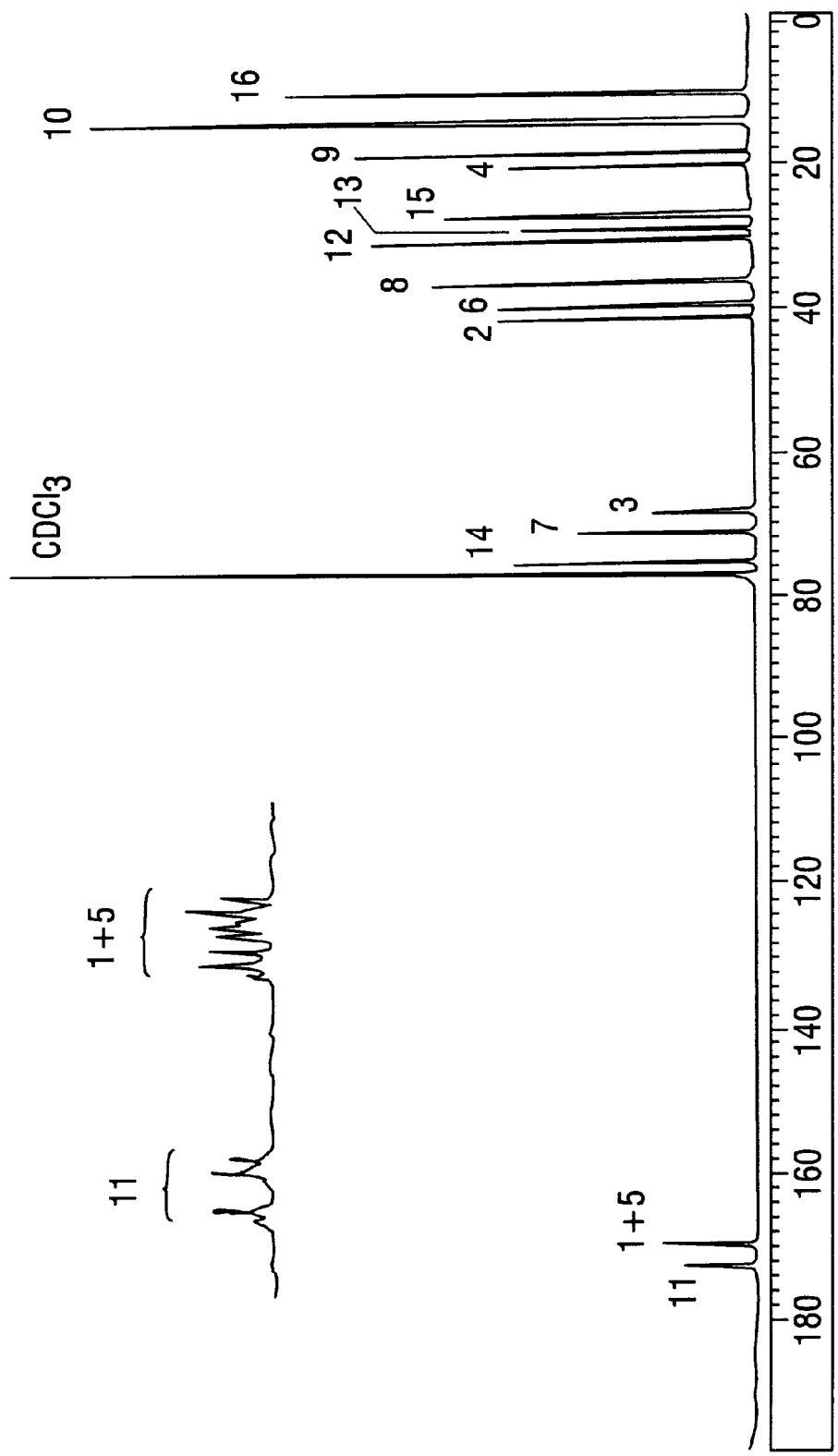
FIG. 15: $^1$H -NMR-spectrum of poly(3HB-co-3HHx-co-4HHx).
Figure 16:
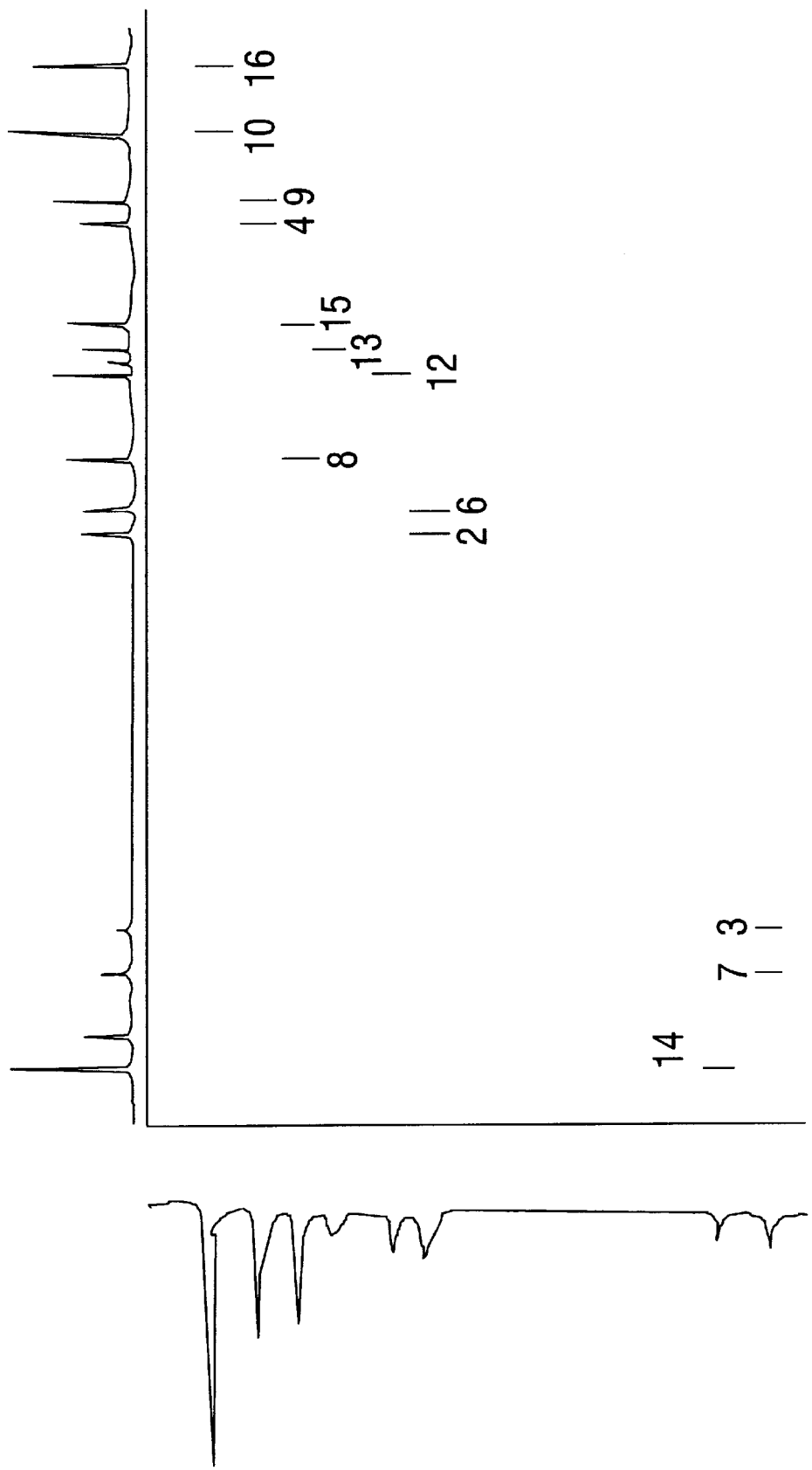
FIG. 16: NMR spectroscopic analysis of poly(3HB-co-3HHx-co-4HHx).
Figure 17:
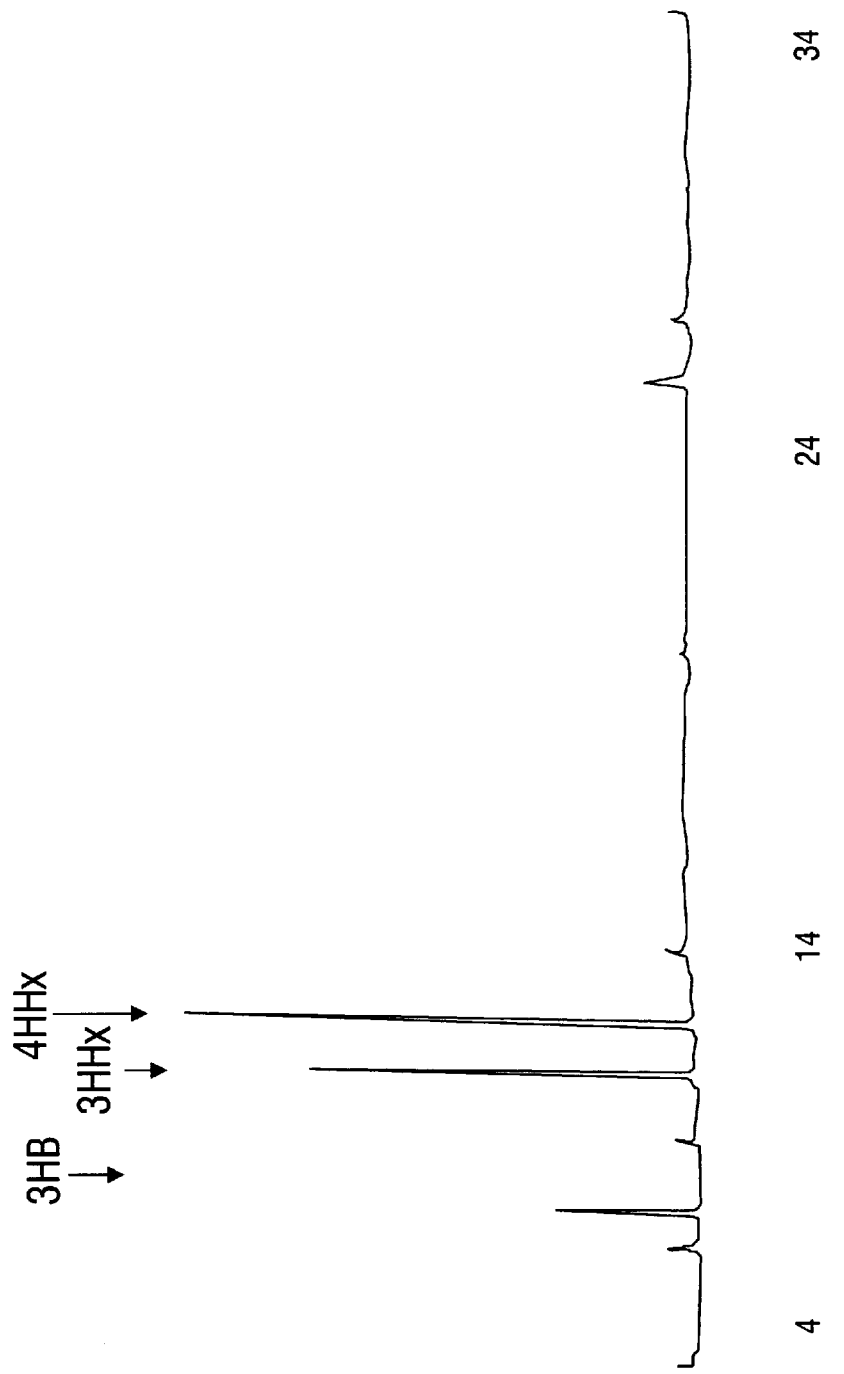
FIG. 17: Gas chromatogram of poly(3HB-co-3HHx-co-4HHx).

In the case of the example, a copolyester of formula poly(3HB-co-3HHx-4HHx) could be prepared whose analytical data are reproduced in the Figures. The polyesters exhibited, for example, the analytical data that are shown in the Figures, whereby FIG. 14 reproduces the $^{13}$C-NMR spectrum and FIG. 15 reproduces the $^1$H-NMR spectrum. The signal assignment is found on the basis of the numbering which is indicated in the structural formula of poly(3HB-co-3HHx-co-4HHx) that is shown in FIG. 13. The gas chromatogram after methanolysis is shown in FIG. 16.

Chemical shift $^{13}$C-NMR signals from poly(3HB-co-3HHx-co-4HHx).

| Monomer | Carbon | Chemical shift [ppm] | |
|---|---|---|---|
| 3HB | 1 | 169.05 | — | 169.89 |
|  | 2 | 40.84 | — | 40.91 |
|  | 3 | 67.32 | — | 67.78 |
|  | 4 | 19.70 | — | 19.83 |
| 3HHX | 5 | 169.05 | — | 169.89 |
|  | 6 | 39.18 | — | 39.41 |
|  | 7 | 70.34 | — | 70.77 |
|  | 8 | 35.96 | — | 36.12 |
|  | 9 | 18.30 | — | 18.34 |
|  | 10 |  |  | 13.73 |
| 4HHX | 11 | 171.91 | — | 172.61 |
|  | 12 | 30.46 | — | 30.50 |
|  | 13 | 28.61 | — | 28.86 |
|  | 14 | 74.66 | — | 74.95 |
|  | 15 | 26.80 | — | 26.95 |
|  | 16 | 9.38 | — | 9.42 |

3HB: 3-hydroxybutyric acid; 3HHx: 3-hydroxyhexanoic acid; 4HHx: 4-hydroxyhexanoic acid.

We claim:

1. An isolated DNA fragment at most 2849 nucleotides in length which encodes a pha E protein and a pha C protein of the *Thiocapsa pfennigii* poly(hydroxy fatty acid) synthase, wherein the DNA fragment comprises nucleotides 180–1280 of SEQ ID NO:1 and nucleotides 1322–2392 of SEQ ID NO:1.

2. An isolated DNA fragment at most 2849 nucleotides in length which encodes a pha E protein of the *Thiocapsa pfennigii* poly(hydroxy fatty acid) synthase, wherein the DNA fragment comprises nucleotides 180–1280 of SEQ ID NO:1.

3. An isolated DNA fragment at most 2849 nucleotides in length which encodes a pha C protein of the *Thiocapsa pfennigii* poly(hydroxy fatty acid) synthase, wherein the DNA fragment comprises nucleotides 1322–2392 of SEQ ID NO:1.

4. An isolated DNA fragment 2849 nucleotides in length which encodes a pha E protein and a pha C protein of the *Thiocapsa pfennigii* poly(hydroxy fatty acid) synthase, wherein the, DNA fragment comprises SEQ ID NO:1.

* * * * *